United States Patent
Maletz et al.

(10) Patent No.: US 11,564,882 B2
(45) Date of Patent: *Jan. 31, 2023

(54) MILLING BLANK FOR PRODUCING AN INDIRECT DENTAL RESTORATION, CORRESPONDING USES AND METHODS

(71) Applicant: VOCO GmbH, Cuxhaven (DE)

(72) Inventors: Reinhard Maletz, Cuxhaven (DE); Nils Fontein, Cuxhaven (DE); Daniel Oldenburger, Cuxhaven (DE); Manfred Thomas Plaumann, Cuxhaven (DE)

(73) Assignee: VOCO GMBH, Cuxhaven (DE)

( * ) Notice: Subject to any disclaimer, the term of this patent is extended or adjusted under 35 U.S.C. 154(b) by 884 days.

This patent is subject to a terminal disclaimer.

(21) Appl. No.: 15/921,120

(22) Filed: Mar. 14, 2018

(65) Prior Publication Data

US 2018/0271629 A1 Sep. 27, 2018

(30) Foreign Application Priority Data

Mar. 17, 2017 (DE) .......................... 102017105841.9

(51) Int. Cl.
| | |
|---|---|
| A61K 9/00 | (2006.01) |
| A61C 13/08 | (2006.01) |
| A61K 6/836 | (2020.01) |
| A61K 6/853 | (2020.01) |
| A61K 6/887 | (2020.01) |
| A61K 6/80 | (2020.01) |
| A61C 5/20 | (2017.01) |
| A61C 5/77 | (2017.01) |
| A61C 5/73 | (2017.01) |
| A61C 13/00 | (2006.01) |
| A61C 13/087 | (2006.01) |
| A61C 13/271 | (2006.01) |

(52) U.S. Cl.
CPC .............. *A61K 9/0024* (2013.01); *A61C 5/20* (2017.02); *A61C 5/73* (2017.02); *A61C 5/77* (2017.02); *A61C 13/0004* (2013.01); *A61C 13/08* (2013.01); *A61C 13/087* (2013.01); *A61C 13/26* (2013.01); *A61K 6/80* (2020.01); *A61K 6/836* (2020.01); *A61K 6/853* (2020.01); *A61K 6/887* (2020.01); *A61C 13/0022* (2013.01)

(58) Field of Classification Search
CPC ...................................................... A61K 6/887
See application file for complete search history.

(56) References Cited

U.S. PATENT DOCUMENTS

| | | | | |
|---|---|---|---|---|
| 4,297,266 | A * | 10/1981 | Ibsen ..................... | A61K 6/887 106/35 |
| 4,544,359 | A * | 10/1985 | Waknine ................. | A61K 6/76 522/14 |
| 6,030,606 | A * | 2/2000 | Holmes .................. | A61K 6/893 424/49 |
| 10,603,143 | B2 * | 3/2020 | Oldenburger ........ | A61C 13/082 |
| 2010/0311862 | A1 | 12/2010 | Engelbrecht | |
| 2012/0129973 | A1 | 5/2012 | Sun | |
| 2012/0302662 | A1 | 11/2012 | Drechsler | |
| 2014/0162216 | A1 * | 6/2014 | Craig ................. | A61C 13/0022 433/201.1 |
| 2014/0200284 | A1 | 7/2014 | Eckert et al. | |
| 2014/0220512 | A1 | 8/2014 | Abuelyaman et al. | |
| 2016/0136059 | A1 | 5/2016 | Hecht et al. | |
| 2017/0035662 | A1 | 2/2017 | Chen | |

FOREIGN PATENT DOCUMENTS

| | | |
|---|---|---|
| DE | 102015220373 | 4/2016 |
| EP | 1143915 | 1/2004 |
| JP | H01275510 | 6/1989 |
| JP | H08056965 | 5/1996 |
| WO | 2010/049522 | 5/2010 |
| WO | 2013/012931 | 1/2013 |

OTHER PUBLICATIONS

Keul et al., "Tensile bond strength of PMMA- and composite-based CAD/CAM materials to luting cements after different conditioning methods", International Journal of Adhesion and Adhesives, 46, 2013, p. 122-127.
Dissertation of Anna Martin, 2015, 101 pages.
Roggendorf et al. "Seven-year clinical performance of CEREC-2 all-ceramic CAD/CAM restorations placed within deeply destroyed teeth", Clin Oral Investig, 2012, 16(5), 1413-1424.
Frankenberger et al., "Leucite-reinforced glass ceramic inlays and onlays after six years: clinical behavior", Oper Dent, 2000, 25(6), 459-465.
Frankenberger et al, "Leucite-reinforced glass ceramic inlays and onlays after 12 years", Adhes Dent ,2008, 10(5), 393-398.
Otto et al., "Computer-aided direct ceramic restorations: a 10-year prospective clinical study of Cerec CAD/CAM inlays and onlays", Int J Prosthodont, 2002, 15(2), 122-128.
Reiss et al., "Clinical results of CEREC inlays in a dental practice over a period of 18 years", Int J Comput Dent, 2006, 9(1), 11-22.
Kassem et al., "Combined effects of thermocycling and load-cycling on microleakage of computer-aided design/computer-assisted manufacture molar crowns", Int J Prosthodont, 2011, 24(4), 376-378.

(Continued)

*Primary Examiner* — Michael F Pepitone
(74) *Attorney, Agent, or Firm* — Duane Morris LLP; Gregory M. Lefkowitz; Brandon A. Chen

(57) ABSTRACT

Described is a milling blank for producing an indirect dental restoration, composed of resin or a resin-based composite, containing water in an amount of at least 25% of the water sorption $W_{sp}$. Described is further a method for producing such a milling blank or a moulded part produced therefrom for use as an indirect dental restoration, a use of the water sorption method, a kit for producing indirect dental restorations and a method for indirect dental restoration.

16 Claims, 2 Drawing Sheets

(56) References Cited

OTHER PUBLICATIONS

Kassem et al., "Fatigue resistance and microleakage of CAD/CAM ce-ramic and composite molar crowns", J Prosthodont, 2012, 21(1), 28-32.

Attia et al., "Fracture load of composite resin and feldspathic all-ceramic CAD/CAM crowns", J Prosthet Dent, 2006, 95 (2), 117-123.

Ramirez-Sebastia et al., "Composite vs Ceramic Computer-aided Design/Computer-assisted Manufacturing Crowns in Endodontically Treated Teeth: Analysis of Marginal Adaptation", Oper Dent, 2013, 38(6), 663-673.

Lauvahutanon et al., "Mechanical properties of composite resin blocks for CAD/CAM", Dent Mater J, 2014, 33(5), 705-710.

Heintze et al., "Crown pull-off test (crown retention test) to evaluate the bonding effectiveness of luting agents", Dental Materials, 2010, 36(3), 193-206.

Bahr et al., "Effect of different adhesives combined with two resin composite cements on shear bond strength to polymeric CAD/CAM materials", Dent Mater J, 2013, 32(3), 492-501.

Güngör et al., "Effect of surface treatments on shear bond strength of resin composite bonded to CAD/CAM resin-ceramic hybrid materials", Adv Prosthodont, 2016, 8, 259-266.

Elsaka et al., "Bond strength of novel CAD/CAM restorative materials to self-adhesive resin cement: the effect of surface treatments", Adhes Dent, 2014, 16(6), 531-540.

Yoshida et al., "Effects of two silane coupling agents, a bonding agent, and thermal cycling on the bond strength of a CAD/CAM composite material cemented with two resin luting agents", J Prosthet Dent, 2001, 85(2), 184-189.

Keul et al., "Impact of different adhesives on work of adhesion between CAD/CAM polymers and resin composite cements", J Dent, 2014, 42(9), 1105-1114.

Stawarczyk et al., "Effect of surface condi-tioning with airborne-particle abrasion on the tensile strength of polymeric CAD/CAM crowns luted with self-adhesive and conventional resin cements", J Prosthet Dent, 2012, 107(2), 94-101.

Gilbert et al., "Effect of the test method on bonding between CAD/CAM high-performance poly-mers and resin-based bonding materials after different pretreatments", Dissertation, Ludwig Maximilian University of Munich, 2014.

Stawarczyk et al., "Long-term tensile bond strength of differently cemented nanocomposite CAD/CAM crowns on dentin abutment", Dental Materials, 2014, 30(3), 334-342.

Basler, "Effect of surface conditioning with air-abrasion on the tensile strength of polymeric CAD/CAM crowns luted with self-adhesive and conventional resin cements", Dissertation, University of Zürich, 2011.

Frankenberger et al., "Adhesive bonding of new CAD/CAM-materials", Int J Comput Dent, 2015, 18(1), 9-20.

Shetty et al., "Resin-Matrix Ceramics—An Overview. International Journal of Recent Scientific Research", 2015, 6(11), 7414-7417.

Vanoorbeek et al., "Computer-aided designed/computer-assisted manufactured composite resin versus ceramic single-tooth restorations: a 3-year clinical study", Int J Prosthodont., 2010, 23(3), 223-230.

Schepke et al., "Clinical Bonding of Resin Nano Ceramic Restorations to Zirconia Abutments: A Case Series within a Randomized Clinical trial" Clin Implant Dent Relat Res, 2016, 18(5), 984-992.

Posselt et al., "Longevity of 2328 chairside Cerec inlays and onlays", Int J Com-put Dent 2003, 6(3), 231-248.

Otto et al., "Long-term clinical results of chairside Cerec CAD/CAM inlays and onlays: a case series", Int J Prosthodont, 2008, 21(1), 53-59.

* cited by examiner

MILLING BLANK FOR PRODUCING AN INDIRECT DENTAL RESTORATION, CORRESPONDING USES AND METHODS

RELATED APPLICATIONS

This application claims priority to German Patent Application No. DE 10 2017 105 841.9, which was filed on Mar. 17, 2017, which is hereby incorporated herein by reference in its entirety.

The present invention relates to a milling blank for producing an indirect dental restoration, a method for producing such a milling blank or a moulded part produced therefrom for use as an indirect dental restoration, a use of the water sorption method, a kit for producing indirect dental restorations and a method for indirect dental restoration.

Indirect dental restorations (also referred to as indirect prosthetic restorations) are used to replace teeth and parts of teeth and comprise in particular moulded pieces selected from the group consisting of an inlay, an onlay, a partial crown, a crown, a veneer and a bridge. The present invention relates to both temporary and permanent restorations, i.e. both temporary and permanent indirect dental restorations.

The term "milling blank" (alternative equivalent terms: "dental milling blank", "dental milling block") refers for the purposes of the present text both to milling blanks composed of resin (and thus comprising no filler) and milling blanks composed of a resin-based composite (also referred to as a "dental composite"). A "resin-based composite" (i.e. a "dental composite material") is understood by the person skilled in the art to be a curable or cured dental composition containing at least one curable liquid or cured solid resin phase and one solid phase dispersed therein, wherein the solid phase can contain fillers of different types and amounts and wherein the curable dental composition can contain one or a plurality of polymerisation initiator(s) and the curable or cured dental composition can optionally contain common additives such as inhibitors, dyes, stabilizers, etc.

A not yet cured (curable) resin or a not yet cured (curable) resin-based composite can be polymerised either chemically and/or thermally and/or photochemically by means of radiation. Milling blanks for producing an indirect dental restoration that are composed of resin or a resin-based composite are known from the prior art. They are particularly suitable and are provided for producing dental prostheses by a CAD/CAM method.

Accompanying technical progress in computer-controlled machines, milling machines have been developed that are capable of producing prosthetic restorations (i.e. indirect dental restorations) with a high degree of precision in the shortest possible time and with a minimum of effort. Against this backdrop, so-called "digital dentistry" was developed. This is currently an area of preeminent and constantly increasing significance in dental technology.

Initially, only ceramic or metal materials were milled, but with the development of resins increasingly well-adapted to the natural dental enamel and resin-based composites, corresponding substances for use as the milling blank also became significant.

With the course of digitisation in modern dentistry, indirect CAD/CAM-produced restorations based on ceramics and resins are becoming increasingly important. While such ceramic-based restorations have already become clinically established, cf. Documents [1-7] below, resin-based composites have also become more important recently. Examples of ceramic materials used include feldspar ceramics, leucite ceramics and lithium disilicate ceramics; however, such ceramic materials have been found to have the drawback of brittleness, resulting in fractures and chipping, cf. Documents [3-4,7-9]. Resins and resin-based composites, particularly resin-based composites for use in CAD/CAM methods, show advantages over ceramic materials because of their high elasticity. Resin-based materials (pure resin or resin-based composites) also show advantages over ceramic materials because they are readily reparable.

Initial comparative in vitro studies of CAD/CAM-produced crowns composed of ceramic and resin-based material (pure resin or a resin-based composite) show that comparable mechanical properties can be achieved with both product classes, cf. Documents [8 through 12]. Until 2010, however, there were virtually no data available on the retention of CAD/CAM-produced resin-based crowns (composed of resin or a resin-based composite) or other resin-based indirect dental restorations. A corresponding review (cf. Document [13] of 2010) states: "No study has investigated into composite or fiber-reinforced composite crowns". In the meantime, with the increasing importance of resin-based CAD/CAM materials, several university working groups have investigated the effect of different parameters on the retention of CAD/CAM-produced restorations, cf. Documents [17 through 21]. For example, the effect of surface pretreatment, the bonding material, and the CAD/CAM material have been investigated. In order to determine retention, shear adhesion bonding tests, (micro)tensile bonding tests, and crown pull-off tests were carried out, with the latter best approximating the clinical situation.

In in vitro studies comparing ceramic and resin-based CAD/CAM-materials (materials for producing indirect dental restorations), ceramic materials were found to show better retention overall:

B. Stawarczyk investigated the tensile strength of adhesively bonded resin-based crowns depending on the bonding system and the bonding composite, cf. Document [22]. Retention was found be poorer than for ceramic crowns tested using the same test design. "The investigated CAD/CAM nano-composite combined with different pre-treatment methods and resin composite cements showed lower tensile bond strength tested with the same laboratory testing assay on dentin abutments compared to zirconia crowns [ . . . ] or glass—ceramic crowns".

T. Basler investigated the tensile bond strength of adhesively bonded CAD/CAM-produced resin-based crowns depending on the pretreatment and the bonding material, cf. Document [23]. Glass ceramic crowns were taken as a control group. In the tests, the ceramic crowns showed significantly higher bonding values than the resin-based crowns: "The adhesively luted glass ceramic crowns [ . . . ] showed the highest tensile strength compared to all other test groups before and after mechanical thermocycling loading" and "In summary, the CAD/CAM resin crowns showed significantly lower tensile strength than the control group."

R. Frankenberger investigated the effect of different pretreatments and different bonding composites on microtensile bond strength, cf. Document [24]. In this study, CAD/CAM materials composed of composites, lithium disilicate ceramics, zirconia-reinforced lithium silicate ceramics and polymer-infiltrated ceramics were compared. The ceramic CAD/CAM materials were found to have the highest bonding values.

These results are confirmed by initial clinical studies. Accordingly, R. Shetty (cf. Document [25]) writes, "Recent studies concluded that Resin Nano Ceramic tends to debond at the luting cement-crown interface especially used in cases of implant single crowns. Since resin matrix ceramics are resilient, elastic deformation occurs within the crown and this stress concentration may be transferred to the adhesive layer leading to debonding issues. The material is no longer considered an indication for crowns".

In a 3-year clinical study, S. Vanoorbeek (cf. Document [26]) observed better survival rates of ceramic crowns (97.2% and 81.2%) compared to resin-based crowns (87.9% and 55.6%).

In a further clinical study on resin-based crowns (cf. Document [27]), resin nanocomposite crowns (RNC) were bonded to two different types of zirconium oxide abutments. After one year, a survival rate of only 14% was observed. The failure was attributed to the resin-based crowns. "For this reason, we hypothesize that the clinical debonding of the RNC crowns in our study might have to do with the RNC material, rather than with the used cement". As a result, it was decided to replace the remaining resin-based crowns with ceramic crowns.

There is therefore a considerable demand for indirect dental restorations composed of resin or resin-based composites that are characterized by particularly favorable retention, preferably retention that is improved over that of the prior art. In the same manner, there is considerable demand for corresponding milling blanks for producing such indirect dental restorations.

There is a corresponding demand for an advantageous method for producing such a milling blank or a moulded part produced therefrom for use as an indirect dental restoration in which the moulded part is produced from the milling blank by milling, preferably by means of a CAD/CAM method.

Furthermore, there is a corresponding demand for an improved method for indirect dental restoration.

A primary object of the present invention was to provide milling blanks for producing an indirect dental restoration showing improved retention. According to further aspects of the present invention, another object was to provide corresponding indirect dental restorations, corresponding methods for producing such a milling blank, a corresponding use of such a milling blank, corresponding kits for producing indirect dental restorations and methods for indirect dental restoration, with the objective always being improved retention.

Improved retention can be evaluated in laboratory tests based on correspondingly favorable bonding values after storage in water in correspondingly designed tests. Such tests are illustrated below in the examples. A specific object of the present invention was to provide milling blanks, etc. that show particularly convincing adhesion properties in such tests, even after storage in water.

Figure 1:
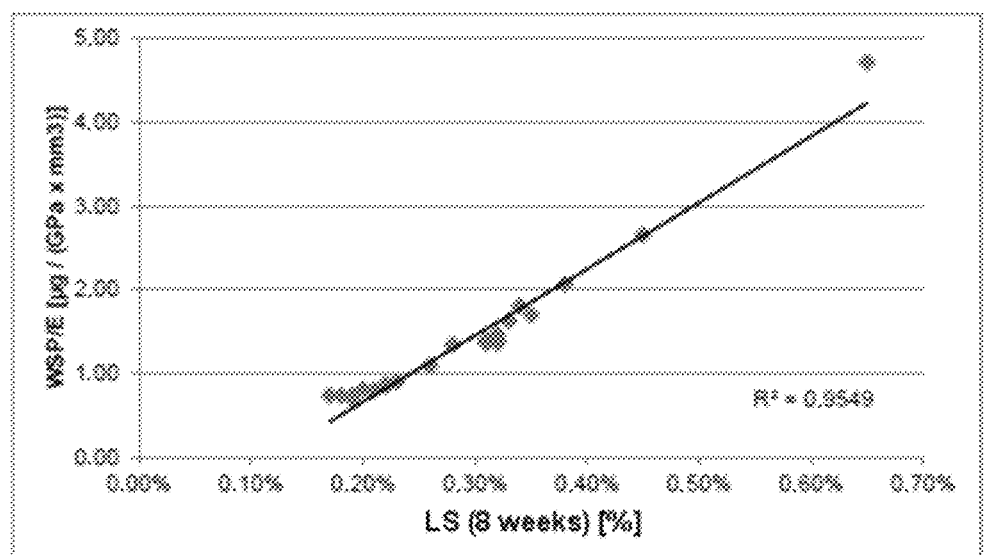
FIG. 1 is a graph of water sorption ($W_{SP}$) over elastic modulus (E) versus linear swelling (LS) of an indirect restoration of the material.

The present invention is based on our own tests, which are described in DE 102017103084.0. It was first found in these tests that the linear swelling (LS) of an indirect restoration is proportional to the water sorption ($W_{SP}$) and inversely proportional to the elastic modulus (E) of the material, cf. FIG. 1. The following equation therefore applies:

$$LS \sim \frac{W_{SP}}{E}$$

This swelling causes a crown to expand, thus increasing the outer and inner diameters thereof, as the entire restoration is enlarged by the swelling. In this case, the relative linear swelling (in percent) is approximately one-third of the relative volume swelling (in percent). The increase in the inner diameter produces a tensile force, which is exerted on the adhesive bond of the bonded crown. If the tensile forces are greater than local adhesion, the bonding material will be torn off and marginal gaps will form at these sites. These sites are thus at increased risk for bacterial colonisation and the formation of secondary caries. If the swelling is sufficiently great or the constant load on the defective sites is sufficiently high, this will result in total retention loss of the restoration.

In order to obtain prosthetic restorations that show stable retention and are free of marginal gaps (indirect dental restorations), it was therefore a specific object of the present invention—based on DE 102017103084.0—to provide milling blanks composed of resin or a resin-based composite that are as free of swelling as possible on storage in water or under conditions such as those prevailing in the oral cavity. Based on the technical teaching of DE 102017103084.0 and particularly the dental milling blanks and materials presented therein, it was a specific object of the present invention to provide milling blanks and indirect dental restorations produced therefrom whose swelling capacity is even further reduced, i.e. that show virtually no swelling.

Based on the technical teaching of DE 102017103084.0, the first considerations in the context of the present invention were directed toward materials whose water sorption is even further reduced, or whose elastic modulus is particularly high. Specifically, according to the proportionality equation shown above, such measures would make it possible to reduce linear swelling, and thus presumably the risk of retention loss.

However, the above-mentioned technical objects were then surprisingly achieved in a completely different manner.

More specifically, it was surprisingly found in our own experiments that the retention of indirect dental restorations (particularly crowns milled from a milling blank by means of CAD/CAM methods) can be considerably improved when milling blanks composed of resin or a resin-based composite, preferably those which have low water sorption capacity per se, are subjected to targeted preconditioning in which the milling blanks sorb water.

While the focus and aim was previously to allow as little water as possible to penetrate into a milling blank composed of resin or a resin-based composite (again see the above-mentioned proportionality equation), in the context of the present invention and thus in diametric opposition to the teaching according to DE 102017103084.0, a milling blank is intentionally produced that already contains a considerable amount of water. In this case, milling blanks that are only minimally capable per se of sorption of water, i.e. show low water sorption $W_{SP}$ (see below for the determination method in the context of the present invention), are preferably used and subjected to the above-mentioned preconditioning. Surprisingly, milling blanks preconditioned in this manner, i.e. milling blanks infiltrated and enriched with water, have an even more significantly reduced swelling capacity than dried milling blanks such as those used e.g. in the test method according to EN ISO 4049:2009 (D) and produced by drying to constant weight.

It is therefore possible by means of the additional step of preconditioning to even further reduce the swelling capacity of milling blanks composed of resin or a resin-based composite and thus to unlock the properties of ceramic milling blanks. In addition, the additional step of preconditioning makes it possible to make substances (resins or resin-based composites) which for material-based reasons show high water sorption $W_{SP}$ and thus high swelling capacity in the dry state and are therefore unsuitable as materials for indirect dental restorations available as materials for milling blanks for producing indirect dental restorations having outstanding retention properties and adhesion properties.

Milling blanks that are preconditioned, i.e. treated and infiltrated with water, composed of resin or a resin-based composite are therefore qualitatively more valuable than corresponding dry milling blanks, and this also enormously increases the number of milling blank types that are well-suited for producing indirect dental restorations. Surprisingly, milling blanks that are preconditioned, i.e. infiltrated with water, composed of resin or a resin-based composite material, provide the clinical retention strength of ceramic blocks without the drawbacks of the latter, such as the tendency toward fractures and chipping. In addition, milling blanks comic) posed of resin or a resin-based composite and the indirect dental restorations produced therefrom can be easily and quickly repaired if needed, in contrast to ceramic milling blanks or indirect dental restorations produced therefrom.

Milling blanks preconditioned with water composed of resin or a resin-based composite are not known in the prior art.

DE 699 22 413 T2 (translation of European Patent specification EP 1 143 915 B1; 3M Innovative Properties Co.) discloses dental milling blanks, comprising (a) a polymeric resin (b) a specific, finally divided filler material, wherein the blank is substantially free of cracks and fabricated such that the blank passes a thermal shock test as specified in more detailed in the document. The document teaches that in certain cases a cured blank is subjected to a specific heat treatment, and that upon completing the heat treatment the blank is allowed to equilibrate to room temperature either by immersion into room temperature water or by slowly cooling via ambient temperature. The immersion into water is not specified in the document, but as it shall serve temperature equilibration it will be only be conducted for a short period of time; a preconditioning in the sense of the considerations stated above will therefore, for physical reasons, not take place. Already here it is referred to table 16 to 18 of the present text from which it can be deduced that water sorption into a milling blank is a particularly slow process. Even at 37° C. (i.e. a temperature significantly above room temperature) it takes several weeks before a degree of conditioning of 25% is reached. It has to be understood that at room temperature the transport processes necessary for water sorption even proceed significantly more slowly so that in time periods necessary for temperature equilibration at room temperature no significant water sorption can occur at all. For corresponding reasons, also at other short-time contact of a milling blank with water (e.g., during milling) there is no significant change of the water content.

The invention is described in the attached claims.

According to a first aspect, the present invention relates to a milling blank for producing an indirect dental restoration composed of resin or a resin-based composite and containing water in an amount of at least 25% of the water sorption $W_{SP}$.

Here, water sorption $W_{SP}$ is a property of the milling blank that is independent of the actual water content. In the framework of the present text and in connection with the present invention, a determination method described below is used to determine water sorption $W_{SP}$ that is quite closely based on the method according to EN ISO 4049:2009 (D). Unless otherwise stated, all data given, particularly experimentally determined values for water sorption $W_{SP}$, refer to the determination method indicated below.

By way of explanation: In this determination method (and this applies analogously to the method according to EN ISO 4049:2009 (D)), a test specimen is dried to constant weight in a first step of the determination method. This dried test specimen is then saturated with water under specified conditions and finally dried again. The water sorption $W_{SP}$—expressed in somewhat simple fashion—is calculated based on (i) the difference between the mass of the test specimen saturated with water and that of the subsequently dried test specimen and (ii) the volume of the test specimen. Based on this method, the water sorption of a test specimen is independent of how low or high the actual water content was before the first drying. By its nature, "water sorption $W_{SP}$" is a value that relates the maximum theoretical amount of water contained in a test specimen to the mass of the dried test specimen.

A milling blank according to the invention is composed of resin or a resin-based composite. Here, the term "milling blank composed of resin" refers to milling blanks that do not contain a filler, while the term "resin-based milling blank" refers in contrast to milling blanks composed of a composite that comprise a resin matrix (i.e. a plastic matrix) and a filler dispersed therein, preferably an inorganic filler.

Milling blanks according to the invention contain water in an amount of at least 25% of the water sorption $W_{SP}$. Concerning determination of water sorption $W_{SP}$, reference is made to the above explanations and the determination method indicated below.

A given milling blank with initially unknown water content contains water in an amount of at least 25% of the water sorption $W_{SP}$, at least in cases where, in drying to constant mass under the other conditions given below, a mass per unit volume (e.g. per millilitre) is lost that corresponds to at least 25% of the mass per unit volume lost on drying of a comparison milling blank that was previously stored in water to constant mass.

A milling blank according to the invention as defined above and in the attached patent claims contains water in an amount of at least 25% of the water sorption $W_{SP}$ (cf. the above remarks and the following explanations concerning the determination method). However, a milling blank according to the invention containing water in an amount of at least 50%, preferably at least 75% and particularly preferably at least 90% of the water sorption $W_{SP}$ is preferred. It was found in our own tests that with increasing water content of the milling blank, there is an increasing positive effect on the retention properties and adhesive behaviour thereof. The person skilled in the art will adjust a milling blank according to the invention with respect to the amount of water contained therein as required in the individual case. If highly specific indirect dental restorations are milled from a milling blank, such as inlays, onlays, partial crowns, crowns, veneers or bridges, there are differing requirements in individual cases with respect to retention and adhesion, and these will be taken into account by the person skilled in the art. In cases of particularly stringent requirements for retention and adhesion, the person skilled in the art will usually prefer a milling blank according to the invention that contains water in an amount of at least 90% of the water sorption $W_{SP}$.

With respect to the aspect of adhesion properties, it is of decisive importance that an indirect dental restoration continues to show favorable adhesion under the conditions prevailing in the oral cavity even after a long period. In the examples below, such conditions are simulated by means of a test in which an idealised crown is bonded to an idealised abutment and the resulting ensemble is then stored for 8 weeks at 37° C. Milling blanks according to the invention always show significantly superior results in such adhesion tests to those of the comparison milling blanks, which contain water in an amount significantly less than 25% of the water sorption $W_{SP}$. The best results are obtained with milling blanks according to the invention that contain water in an amount of at least 90% of the water sorption $W_{SP}$.

Although milling blanks according to the invention show significantly improved properties (more particularly, improved retention and improved adhesion after bonding and storage in water) in respective comparison with milling blanks containing water in an amount sharply less than 25% of the water sorption $W_{SP}$, it is also useful, in order to achieve particularly advantageous absolute values, to adjust the other physical parameters of a milling blank according to the invention based on the considerations associated with Document DE 102017103084.0.

Preferred is therefore a milling blank according to the invention, preferably of the type described above as preferred, containing water in an amount of at least 90% of the water sorption $W_{SP}$, with an E modulus, determined according to ADA Specification No. 27—1993, of at least 10 GPa, preferably at least 13 GPa and particularly preferably at least 15 GPa. The person skilled in the art will usually set the desired E modulus of a milling blank according to the invention by selecting the type and amount of the fillers and monomers used, and optionally, the curing method selected and the like.

In this respect, it should be taken into account that our own tests have shown that the E modulus of a milling blank does not depend to a significant degree on the amount of water contained therein. As discussed above, according to our own tests, the linear swelling (LS) of an indirect dental restoration follows a course that is roughly inversely proportional to the E modulus. As the retention properties and the adhesion properties frequently depend directly on linear swelling, milling blanks according to the invention with a high E modulus (as discussed above) are particularly advantageous.

A milling blank according to the invention, preferably a milling blank according to the invention as described above as preferred, and more particularly a milling blank according to the invention containing water in an amount of at least 90% of the water sorption $W_{SP}$ and/or with an E modulus of at least 10 GPa and preferably at least 15 GPa, preferably has a water sorption $W_{SP}$ of at most 40 µg/mm³, preferably at most 30 µg/mm³ and particularly preferably at most 20 µg/mm³.

As discussed above, linear swelling is approximately proportional to water sorption $W_{SP}$ (as defined above; see below for determination method). Milling blanks according to the invention with a water sorption of at most 40 µg/mm³, preferably at most 30 µg/mm³ and particularly preferably at most 20 µg/mm³ therefore show particularly outstanding retention properties and adhesion properties (especially after bonding and after storage in water or the oral cavity).

Particularly preferred are milling blanks according to the invention for producing an indirect dental restoration (composed of resin or a resin-based composite) that contain water in an amount of at least 90% of the water sorption $W_{SP}$, with an E modulus of at least 13 GPa (preferably at least 15 GPa) and a water sorption $W_{SP}$ of at most 20 µg/mm³.

In view of the correlation determined in our own tests between linear swelling and the quotients of water sorption $W_{SP}$ and the E modulus, milling blanks according to the invention in which the quotient of the water sorption $W_{SP}$ (as defined above; see below for determination method) and the E modulus determined according to ADA Specification No. 27—1993 is less than 1.35 µg/(GPa×mm³), and preferably less than 1.00 µg/(GPa×mm³), are particularly preferred.

Our own tests, a summary of which is presented below, confirm that particularly outstanding results are obtained with the preferred milling blanks according to the invention (with preferred E modulus values, water sorption and quotients of water sorption $W_{SP}$ and E modulus), especially for adhesion after bonding and storage in water.

Particularly preferred is a milling blank according to the invention for producing an indirect dental restoration composed of resin or a resin-based composite containing water in an amount of at least 50%, preferably at least 75% and particularly preferably at least 90% of water sorption $W_{SP}$ and/or with an E modulus determined according to ADA Specification No. 27—1993 of at least 10 GPa, preferably at least 13 GPa and particularly preferably at least 15 GPa and/or with water sorption $W_{SP}$ of at most 40 µg/mm³, preferably at most 30 µg/mm³ and particularly preferably at most 20 µg/mm³ and/or wherein the quotient of the water sorption $W_{SP}$ and the E modulus determined according to ADA Specification No. 27—1993 is less than 1.35 µg/(GPa×mm³) and preferably less than 1.00 µg/(GPa×mm³); here, the conjunction "and" is preferably applied in each case. In addition, two or more of the strictest (narrowest) definitions are preferably combined with one another (90% water sorption $W_{SP}$; E modulus of at least 15 GPa; water sorption $W_{SP}$ of at most 20 µg/mm³; quotient preferably less than 1.00 µg/GPa×mm³). All of these strictest (narrowest) definitions are preferably combined with one another. Corresponding milling blanks are particularly preferred because of their highly outstanding retention properties and adhesion properties.

Most particularly preferred is a milling blank according to the invention as defined above (preferably a milling blank according to the invention as described above as preferred or particularly preferred) wherein the difference between the water sorption $W_{SP}$ and water content of the milling blank (determined by drying under the conditions specified below, differential weighing and volume determination) is less than 10 µg/mm³, preferably less than 8 µg/mm³ and particularly preferably less than 4 µg/mm³.

Said difference corresponds to the water sorption capacity remaining after preconditioning of the preconditioned milling blank according to the invention. A milling blank for which the difference is determined to be less than 10 µg/mm³ can only contain less than 10 µg of water per mm³ of the milling blank at a minimum temperature of 37° C. Accordingly, such a preferred milling blank according to the invention has virtually no remaining swelling capacity. Crowns produced from such a milling blank show outstanding adhesion values in corresponding tests after bonding to an abutment, even after long-term storage in water.

A particular merit of the present invention is the provision of (preconditioned) milling blanks that can (additionally) sorb not more than 10 µg of water per mm³ milling blank (preferably less than 8 µg/mm³, preferably less than 4 µg/mm³). Such milling blanks are not known from the prior art.

If the water sorption $W_{SP}$ of a given milling blank is high, a considerable amount of water must be added to such a milling blank so that said difference is less than 10 µg/mm³ (preferably less than 8 µg/mm³ and more preferably less than 4 µg/mm³). In contrast, if the water sorption $W_{SP}$ of a given milling blank is already very low (for example 12 µg/mm³, cf. Example 4 below with respect to this example), this milling blank must sorb only relatively small amounts of water, such that the difference between the water sorption $W_{SP}$ and water content of the milling blank is less than 10 µg/mm³, preferably less than 8 µg/mm³, and most preferably less than 4 µg/mm³.

Particularly preferred is a milling blank according to the invention composed of a resin-based composite, comprising
   a) an inorganic filler in an amount of at least 70 wt. %, preferably at least 80 wt. %, based on the total mass of the milling blank
   and
   b) a resin matrix (plastic matrix).

In addition to the inorganic filler and the resin matrix, such a preferred milling blank according to the invention may also contain trace amounts of initiators for curing and other additives. A milling blank according to the invention composed of a resin-based composite, which contains an inorganic filler in the above-mentioned preferred amount and a resin matrix, is advantageously configured in the manner described above as preferred with respect to the amount of water contained, the E modulus, the water sorption $W_{SP}$ and/or the quotients of the water sorption $W_{SP}$ and the E modulus.

Preferably, a preferred milling blank according to the invention is composed of a resin-based composite which comprises an inorganic filler in the above-mentioned amount and a resin matrix, configured such that the inorganic filler a) comprises:
   a1) a glass composition and
   a2) non-aggregated and non-agglomerated silica with an average particle size of not more than 80 nm (see below for measuring method).

Particularly advantageous, therefore, is a milling blank according to the invention, wherein the glass composition a1) comprises
   a first glass composition a1a) with a D50 value in the range of 0.4 to 1.0 µm, preferably in the range of 0.5 to 0.9 µm,
   and
   a second glass composition a1b) with a D50 value in the range of 1.2 to 5.0 µm, preferably in the range of 1.5 to 4.0 µm,
   wherein the mass ratio of a1a) to a1b) is between 1:1.5 and 1:8, preferably between 1:2 and 1:5,
   wherein the mass ratio of a2) to the total of a1a) and a1b) is between 1:3 and 1:6,
   wherein the ratio of the D50 value of the first glass composition a1a) to the D50 value of the second glass composition a1b) is in the range of 1:1.5 to 1:10, preferably 1:2 to 1:5,
   and wherein the D75 value of the first glass composition a1a) is less than the D25 value of the second glass composition a1b).

In milling blanks according to the invention composed of a resin-based composite that comprise an inorganic filler a) and a resin matrix b), the resin matrix can account for up to 30 wt. % based on the total mass of the milling blank. Frequently, however, in addition to the components of the inorganic filler a) and the resin matrix b), one or a plurality of further components are also provided that can be allocated neither to the inorganic filler nor to the resin matrix, for example residues of initiators for curing and other additives, possibly including organic fillers.

A preferred milling blank according to the invention is composed of a resin-based composite and comprises
   a) an inorganic filler in an amount of at least 70 wt. %, preferably at least 80 wt. %, based on the total mass of the milling blank.
   and
   b) a resin matrix,
   wherein the inorganic filler a) comprises:
   a1) a glass composition and
   a2) non-aggregated and non-agglomerated silica with an average particle size of not more than 80 nm,
   wherein the glass composition a1) comprises
   a first glass composition a1a) with a D50 value in the range of 0.4 to 1.0 µm, preferably in the range of 0.5 to 0.9 µm,
   and
   a second glass composition a1b) with a D50 value in the range of 1.2 to 5.0 µm, preferably in the range of 1.5 to 4.0 µm,
   wherein the mass ratio of a1a) to a1b) is between 1:1.5 and 1:8, preferably between 1:2 and 1:5,
   wherein the mass ratio of a2) to the total of a1a) and a1b) is between 1:3 and 1:6,
   wherein the ratio of the D50 value of the first glass composition a1a) to the D50 value of the second glass composition a1b) is in the range of 1:1.5 to 1:10, preferably 1:2 to 1:5,
   and wherein the D75 value of the first glass composition a1a) is less than the D25 value of the second glass composition a1b).

Particularly preferred in this case are configurations in which several or all of the strictest (narrowest) definitions are combined with one another, i.e.: at least 80 wt. % of inorganic filler; D50 value of the first glass composition a1a) is in the range of 0.5 to 0.9 µm; D50 value of the second glass composition a1b) is in the range of 1.5 to 4.0 µm; mass ratio of a1a) to a1b) is between 1:2 and 1:5; and ratio of the D50 value of the first glass composition a1a) to the D50 value of the second glass composition a1b) is in the range of 1:2 to 1:5. Of course, these preferred configurations are also adjusted or selected in the preferred manner with respect to water content (preferably at least 90% of the water sorption $W_{SP}$), E modulus values (preferably at least 15 GPa), water sorption $W_{SP}$ (preferably at most 20 µg/mm³) and/or the quotients of water sorption $W_{SP}$ and E modulus (preferably less than 1.00 µg/GPa×mm³).

Preferred is a milling blank according to the invention that comprises a) an inorganic filler in an amount of at least 70 wt. %, preferably at least 80 wt. %, based on the total mass of the milling blank and b) a resin matrix, wherein the resin matrix b) is a polymer of monomers that contain difunctional (meth)acrylates and wherein the percent by weight of ethoxylated bisphenol A dimethacrylate with an average degree of ethoxylation of 2 to 4 ethoxy groups per molecule is greater than 40 wt. % and less than 50 wt. %, based on the total mass of the monomers.

Such a milling blank is produced using a monomer mixture containing difunctional (meth)acrylates in which the percent by weight of ethoxylated bisphenol A dimethacrylate with an average degree of ethoxylation of 2 to 4 ethoxy groups per molecule in the monomer mixture is greater than 40 wt. % and less than 50 wt. %, based on the total mass of the monomers. After mixing of the monomer mixture, one or a plurality of initiators for curing, and optionally present additives with the required amount of inorganic filler, curing of the monomer mixture is carried by polymerisation to the resin matrix b) in the usual manner, e.g. by means of radiation curing (photochemically) and/or chemical curing (redox reaction) and/or thermally.

The use of ethoxylated bisphenol A dimethacrylate with an average degree of ethoxylation of 2 to 4 ethoxy groups per molecule in the indicated amount results in particularly favorable results in adhesion tests, and in practice, in particularly favorable retention of corresponding indirect dental restorations. With respect to a comparison of the properties of milling blanks according to the invention depending on the degree of ethoxylation of the amounts of ethoxylated bisphenol A used, reference is made to Examples 9 to 12 and Tables 6 and 7 referring thereto.

A milling blank according to the invention is suitable and provided for producing an indirect dental restoration. Preferably, the dimensions of the milling blank according to the invention are selected such that a cube with an edge length of 10 mm, preferably 14 mm, and/or a cuboid having a square base with an edge length of 10 mm, preferably 14 mm, and a height of 20 mm can be milled from it.

It has to be noted that in industrial practice any laboratory analysis or examination regarding water sorption etc. was routinely not conducted on milling blanks but on test specimen having significantly smaller dimensions, e.g. thin slices. Such test specimen regularly or typically are no milling blanks within the meaning of the present invention, because they are not suitable for producing an indirect dental restoration, and they do not possess the preferred dimensions as stated above.

Correspondingly dimensioned milling blanks according to the invention are suitable for use in producing an inlay, an onlay, a partial crown, a crown, a veneer or a bridge.

In the following, preferred components of milling blanks according to the invention or curable mixtures are given from which the milling blanks according to the invention can be produced.

a) Inorganic Fillers:

The milling blank according to the invention contains inorganic fillers in an amount of at least 70 wt. %, preferably at least 80 wt. %, based on the total mass of the milling blank, and accordingly, curable mixtures for producing a milling blank according to the invention contain inorganic fillers in an amount of at least 70 wt. %, preferably at least 80 wt. %, based on the total composition of the mixture. Inorganic fillers are preferably used as a mixture of various filler fractions; in order to optimise product properties, inorganic fillers are included in the formulations with differing particle sizes, wherein they preferably show a multimodal distribution and particularly preferably a bimodal distribution.

Depending on the requirements in the individual case, inorganic fillers in the form of compact glasses and/or in the form of various silicas of different sizes and states (monodisperse, polydisperse) are preferred as components of milling blanks according to the invention and corresponding premixtures.

Examples of suitable inorganic components are amorphous materials based on mixed oxides of $SiO_2$, $ZrO_2$ and/or $TiO_2$ and fillers such as quartz glass ceramics or glass powder, barium silicate glasses, barium fluorosilicate glasses, strontium silicate glasses, strontium borosilicate glasses, Li/Al silicate glasses, barium glasses, calcium silicates, sodium aluminium silicates, fluoroaluminium silicate glasses, oxides of aluminium or silicon, zeolites, apatite, zirconium silicates, sparingly soluble metal salts such as barium sulfate or calcium fluoride, and radiopaque fillers such as ytterbium fluoride.

A milling blank according to the invention preferably contains barium aluminium borosilicate glasses as a component of the filler component a).

In order to improve incorporation into the resin matrix (plastic matrix; polymer matrix), the above-mentioned materials can be organically surface-modified; this is preferred in many cases. As an example, one can mention surface treatment of inorganic fillers with a silane. Methacryloxypropyl trimethoxysilane is particularly suitable as a coupling agent.

A milling blank according to the invention preferably contains surface-treated barium aluminium borosilicate glasses, preferably silanised barium aluminium borosilicate glasses and most preferably barium aluminium borosilicate glasses treated with methacryloxypropyl trimethoxysilane.

Preferably, and depending on the requirements in the individual case, different silicas are used in the milling blanks according to the invention.

As mentioned above in connection with the component a2), milling blanks according to the invention preferably contain nanoscale silicic acids, i.e. silicic acid particles with an average particle size of not more than 80 nm. These silicas are preferably non-aggregated and nonagglomerated. Production of the nanoscale silicas is carried out in a known manner, for example by flame pyrolysis, plasma methods, gas phase condensation, colloid techniques, precipitation methods, sol-gel methods, etc.

If the nanoscale silicas are in non-agglomerated and non-aggregated form, they should preferably be in monodisperse form. This is particularly preferred. In order to allow favorable incorporation of the nanoparticles (particles with an average particle size of not more than 80 nm) in the resin matrix (polymer matrix; plastic matrix) of a radically curable dental composition for producing a milling blank according to the invention, the surfaces of the nanoscale silicas are preferably organically surface-modified, i.e. their surfaces show organic structural elements. As an example, one can again mention surface treatment of the fillers with a silane. Methacryloxypropyl trimethoxysilane is also particularly well-suited as a coupling agent for said nanoparticles.

A milling blank according to the invention particularly preferably contains surface-treated nanoscale non-agglomerated and non-aggregated silica particles with an average particle size of not more than 80 nm, preferably silanised nanoscale non-agglomerated and non-aggregated particles with an average particle size of not more than 80 nm and most preferably nanoscale non-agglomerated and non-aggregated silica particles with an average particle size of not more than 80 nm treated with methacryloxypropyl trimethoxysilane.

Commercially available nanoscale non-agglomerated and non-aggregated silica sols that can be preferably used in producing a milling blank according to the invention include those referred to in the market as "NALCO COLLOIDAL SILICAS" (Nalco Chemical Co.) "Ludox colloidal silica" (Grace) or "Highlink OG" (Clariant).

The filler portion of a milling blank according to the invention preferably contains a mixture of a2) non-aggregated and non-agglomerated silica with an average particle size of not more than 80 nm and a second filler in the form of microparticles with an average particle size in the range of 0.4 µm to 5 µm. This second filler is preferably the glass composition of a milling blank according to the invention defined above as component a1). By combining nanoparticles, i.e. non-aggregated and non-agglomerated silica with an average particle size of not more than 80 nm, with microparticles (preferably microparticles of a glass composition, cf. a1) above), particularly complete and homogeneous volume filling of the milling blank according to the invention is achieved.

Within a corresponding milling blank according to the invention, the microparticles cause largely homogenous filling of the volume, wherein the remaining empty spaces between the microparticles are at least partially filled by the above-described nanoparticles (component a2)). In the context of the present invention, the term microparticles is understood to mean particles with an average particle size of 400 nm to 5 µm. The use of glass compositions as microparticles is preferred.

If microparticles are contained in the inorganic filler a) of a preferred milling blank according to the invention (preferably microparticles of a glass composition a1)), these microparticles preferably show a bimodal particle size distribution. Microparticles with a bimodal particle size distribution are preferred because more complete volume filling can be achieved with these particles than in use of microparticles with a monomodal particle size distribution. In the case of a bimodal particle size distribution, the particles of the fractions with the larger particle size result in coarse filling of the volume, while the particles of the fraction with the smaller particle size, to the extent possible, will fill the spaces between the particles of the fractions with the larger particle size. Any remaining empty spaces will then be filled by nanoparticles as deli) scribed above.

The use of a mixture of two microparticle fractions is preferred, wherein a first microparticle fraction has a D50 value in the range of 0.4 to 1.0 µm, and preferably in the range of 0.5 to 0.9 µm. This is preferably a first glass composition a1a) (see above for preferred configurations). The second microparticle fraction has a D50 value in the range of 1.2 µm to 5.0 µm, and preferably in the range of 1.5 µm to 4.0 µm. This is preferably a second glass composition a1b) as defined above (see above for preferred configurations).

The ratio of the total mass of such a first microparticle fraction to the total mass of such a second microparticle fraction is preferably in the range of 1:1.5 to 1:8, preferably in the range of 1:2 to 1:5. This applies in particular if the first microparticle fraction is a first glass composition a1a) and the second microparticle fraction is a second glass composition a1b).

b) Resin Matrix (Plastic Matrix, Polymer Matrix) and Monomers for Producing Such a Resin Matrix:

A milling blank according to the invention for producing an indirect dental restoration composed of resin or a resin-based composite. For producing the cured resin or the resin matrix (plastic matrix; polymer matrix that constitutes the resin component of the resin-based composite), radically polymerisable monomers are used as components of a radically curable composition that additionally contains an inorganic filler of component a) and optionally further components. The proportion of the polymer of radically polymerisable monomers in a milling blank according to the invention is preferably not greater than 30 wt. %, as an inorganic filler is preferably present in an amount of at least 70 wt. % (see above). The same applies to the radically curable composition, in which the radically polymerisable monomers are used in addition to fillers.

The radically polymerisable monomers are preferably the (meth)acrylate monomers commonly used in dental chemistry in composite materials. In this case, a corresponding polymer comprises a corresponding poly(meth)acrylate.

Numerous compounds are mentioned in the patent literature (for example in the document DE 3941629 A1), all of which are diesters of acrylic or methacrylic acid and are suitable for producing a resin or a resin matrix of a resin-based composite such as that contained in a milling blank according to the invention.

In a preferred embodiment of a milling blank according to the invention, the milling blank comprises a resin matrix that is produced by polymerisation of one or a plurality of monomers selected from the group composed of ethylene glycol dimethacrylate (EGDMA), 1,6-hexanediol dimethacrylate (HDDMA), triethylene glycol dimethacrylate (TEGDMA), 1,10-decanediol dimethacrylate (DEDMA), 1,12-dodecanediol dimethacrylate (DODMA), ethoxylated bisphenol A dimethacrylate, ethoxylated bisphenol A dimethacrylate, wherein the bisphenol is reacted with 2 to 4 mol of ethylene oxide and the intermediate product is then saturated with 2 mol of methacrylic acid, polyethylene glycol dimethacrylate (PEGDMA), 7,7,9-trimethyl-4,13-dioxo-3,14-dioxa-5,12-diazahexadecane-1,16-dioxydimethacrylate (UDMA), butanediol dimethacrylate, tetraethylene glycol dimethacrylate, neopentyl glycol dimethacrylate and bisphenol Aglycidyl-methacrylate (bis-GMA).

Specifically preferred are the corresponding dimethacrylates or diacrylates of the dihydroxymethyltricyclo[$5.2.1.0^{2,6}$]decanes, as described in the documents DE 1816823, DE 2419887, DE 2406557, DE 2931926, DE 3522005, DE 3522006, DE 3703120, DE 102005021332, DE 102005053775, DE 102006060983, DE 69935794 and DE 102007034457.

c) Initiators:

Preferred milling blanks according to the invention can be produced by radiation curing (photochemically) and/or by chemical curing (redox reaction) and/or by thermal curing of a corresponding composition, wherein the composition contains as component a) an inorganic filler in an amount of at least 70 wt. %, preferably at least 80 wt. %, based on the total mass of the milling blank produced and/or the compositions used or is a filler-free composition for producing a milling blank composed of resin. Preferred according to the invention for producing a milling blank is thermal curing of a corresponding composition, wherein the thermal curing is carried out, for example, by means of peroxide decomposition.

Examples of suitable photosensitizers are α-diketones, benzoin alkyl ethers, thioxanthones, benzophenones, acylphosphine oxides, acyl germanium compounds, acetophenones, ketals, titanocenes, sensitising dyes, etc. The sensitisers may be used alone or in combination. Specific example of substances of these various classes are found for example in DE 102006019092 A1 or in DE 3941629 C2.

Examples of accelerators that are used together with the sensitisers are tertiary amines, secondary amines, barbituric acids, tin compounds, aldehydes and sulphur compounds.

Specific examples of substances of these various classes are found in DE 102006019092 or in DE 3941629 C2.

Further suitable initiators and initiator combinations are described in DE 60116142.

Suitable photoinitiators are characterized in they can cause curing of a radically curable dental composition by absorbing light in the wavelength range of 300 nm to 700 nm, preferably 350 nm to 600 nm and particularly preferably 380 nm to 500 nm, optionally in combination with one or a plurality of coinitiators that can induce curing of a radically curable dental composition.

The absorption maximum of camphorquinone (CQ) is approx. 470 nm and is thus in the range of blue light. Camphorquinone (CQ) is one of the $PI_2$ initiators and is commonly used in combination with a coinitiator.

A suitable catalyst system contains the combination of an α-diketone and an aromatic tertiary amine, with the combination of camphorquinone (CQ) and ethyl-p-N,N-dimethylaminobenzoate (DABE) being preferred.

Also preferred is the further combination of the system "α-diketone/aromatic tertiary amine" with a phosphine oxide, particularly phenyl-bis(2,4,6-trimethylbenzoyl)phosphine oxide and/or 2,4,6-trimethylbenzoyl diphenyl phosphine oxide. With respect to the structures of suitable phosphine oxides, reference is made to the documents DE 3801511 C2, DE 102006050153 A1, EP 0184095 B1, DE 4231579 C2, EP 0366977 B1, U.S. Pat. No. 7,081,485 B2, DE 3236026 A1, US 2007/0027229 A1, EP 0262629 B1, EP 0073413, U.S. Pat. No. 7,148,382 B2, U.S. Pat. No. 5,761,169, DE 19708294 A1, EP 0057474, EP 0047902 A, EP 0007508, DE 60029481 T2, EP 0980682 B1, EP 0948955 B1, EP 1236459 B1 and EP 0173567 A2.

The phosphine oxides mentioned in these documents are particularly suitable alone or in combination with the system "α-diketone/amine" as a photopolymerisation initiator system.

Further suitable photoinitiators are described in J.-P. Fouassier, Photoinitiation, Photopolymerization and Photocuring, Hanser Publishers, Munich, Vienna, N.Y. 1995 and in J. F. Rabek (Eds.), Radiation Curing in Polymer Science and Technology, Vol. II, Elsevier Applied Science, London, N.Y. 1993.

A variety of initiators for chemical curing is known to the person skilled in the art. In this context, reference is made by way of example to EP 1720506. Initiators for chemical curing are also described in the above-mentioned documents DE 102006019092 and DE 3941629.

Preferred initiators for chemical curing are dibenzoyl peroxide and dilauroyl peroxide, particularly dibenzoyl peroxide in combination with amines such as N,N-dimethyl-p-toluidine, N,N-dihydroxyethyl-p-toluidine and structurally related amines.

Dual-curing systems comprise a combination of photoinitiators and initiators for chemical curing.

In addition to the oxidatively active organic peroxide compounds, barbituric acids or barbituric acid derivatives and malonyl sulfamide can also be used as redox systems.

Among the barbituric acid systems, the so-called "Bredereck systems" are highly significant. Examples of suitable "Bredereck systems" and references to the relevant patent literature can be found in EP 1839640 and in DE 1495520, WO 02/092021 or WO 02/092023.

Instead of the barbituric acids, salts thereof can also be used. Examples thereof are found in the following documents: EP 1872767, EP 2070506, EP 1881010, DE 102007050763, U.S. Pat. No. 6,288,138, DE 112006001049, U.S. Pat. No. 7,214,726 and EP 2070935.

Suitable malonyl sulfamides are described in EP 0059451. Preferred compounds in this connection are 2,6-dimethyl-4-isobutyl malonyl sulfamide, 2,6-diisobutyl-4-propyl malonyl sulfamide, 2,6-dibutyl-4-propyl malonyl sulfamide, 2,6-dimethyl-4-ethyl malonyl sulfamide and 2,6-dioctyl-4-isobutyl malonyl sulfamide.

Furthermore, sulphur compounds with oxidation states of +2 or +4 such as sodium benzenesulfinate or sodium p-toluenesulfinate can be used.

In order to accelerate curing, polymerisation can be carried out in the presence of compounds of heavy metals such as Ce, Fe, Cu, Mn, Co, Sn or Zn, wherein copper compounds are particularly preferred. The heavy metal compounds are preferably used in the form of soluble organic compounds. In this connection, preferred copper compounds are copper benzoate, copper acetate, copper ethylhexanoate, copper di(methacrylate), copper acetylacetonate and copper naphthenate.

When peroxides are heated, they decompose and form free radicals, which are capable of initiating polymerisation. The most widespread system for thermal polymerisation is the use of dibenzoyl peroxide. Further thermal initiators are ketone peroxides, peroxy ketals, hydroperoxides, dialkyl peroxides, diacyl peroxides, peroxyesters and peroxydicarbonates such as dicumyl peroxide, chlorobenzoyl peroxide, t-butylperbenzoate, dilauroyl peroxide, cumene hydroperoxide, 3,5,5-trimethylhexanoic acid-tert-butylperoxyester and azo compounds such as 2,2'-azobisisobutyronitrile, 2,2'-azobis-2,4-dimethylvaleronitrile, 2,2'-azobis-1-cyclohexanecarbonitrile or dimethyl-2-2'-azobisisobutyrate. Substances such as sodium or potassium persulfate also thermally decompose and are suitable compounds in this connection. These substances can be used individually or in mixtures with one another. For this purpose, the radically curable dental compositions only need to be heated to the decomposition temperature of the respective peroxides indicated by the manufacturer. The radically curable compositions are advantageously heated to a temperature above the decomposition temperature and kept at said temperature for a time so that the polymer has the time required for relaxation. The person skilled in the art determines the optimum temperature by successively increasing the temperature for curing up to the point at which the polymer no longer shows any substantial improvements in its important measured parameters, such as flexural strength, E modulus and water sorption.

Preferably, thermal curing is carried out in such a way that the radically curable composition is transferred into a block mould, in which it is cured at temperatures of 80° C. to 150° C. and a pressure of 100 to 300 bar.

d) Additives:

In many cases, a milling blank according to the invention comprises one or a plurality of further(s) additive(s).

These additives can have various functions. Common additives for use in dental materials are known to the person skilled in the art, who will select the suitable additives depending on the function desired. In the following, typical additives and their functions are described by way of example.

UV absorbers, which for example are capable of absorbing UV radiation due to their conjugated double bonding systems and aromatic rings, are in many cases components of a milling blank according to the invention. Examples of UV absorbers are 2-hydroxy-4-methoxybenzophenone, salicylic acid phenyl esters, 3-(2'-hydroxy-5'-methylphenyl)benzotriazole and diethyl-2,5-dihydroxyterephthalate. The polymers contain these additives in order to ensure colour stability.

As the purpose of indirect dental restorations is to restore teeth in a manner as close to nature as possible, it is necessary to provide the milling blanks according to the invention in a variety of colour tones. For this purpose, as a rule, milling blanks according to the invention contain inorganic and/or organic pigments, preferably in amounts that are minimal, but sufficient for the aforementioned purposes.

Further optional additives are dental pharmaceuticals and microbicidal agents, preferably bactericidal agents or fluorescent agents, which are also used to simulate the natural appearance of teeth.

A milling blank according to the invention contains an unusually high amount of water, which is ordinarily incorporated into the milling blank by means of corresponding preconditioning. In storage of a milling blank according to the invention, as this amount of water should preferably not decrease significantly, it is preferable to take measures to prevent the milling blank from losing water in an undesirable manner. There are therefore a number of measures available to the person skilled in the art, ranging from storage in contact with water and surface sealing of a milling blank according to the invention, e.g. by infiltration and curing of monomers, to water-tight enclosure of the milling blank.

Preferred is a milling blank according to the invention (as defined above, preferably as referred to above as preferred or particularly preferred) wherein the milling blank is sealed or enclosed in a water-tight manner, preferably enclosed in a water-tight manner by a water-tight container, preferably a blister and/or a water-tight lacquer and/or a water-tight wax sheath.

For the purposes of the present text, the term "water-tight" means that a milling blank according to the invention that is sealed or enclosed in a "water-tight" manner, at a storage temperature of 25° C. and an ambient pressure of 1013 hPa with a relative humidity of 30%, still contains water in an amount of at least 25% of the water sorption $W_{SP}$, i.e. is still in accordance with the invention, even after storage for a year.

A preferred milling blank according to the invention (with a correspondingly high water content) can preferably even be sealed or enclosed in a water-tight manner to such an extent that even after a year under the storage conditions indicated, it still contains water in an amount of at least 50%, preferably at least 75% and particularly preferably at least 90% of the water sorption $W_{SP}$.

The present invention also relates to the use of a milling blank according to the invention for producing a moulded part for use as an indirect dental restoration, preferably a moulded part selected from the group consisting of an inlay, an onlay, a partial crown, a crown, a veneer and a bridge. As discussed above, a moulded part is preferably produced by milling from a milling blank according to the invention.

The present invention also relates to a method for producing a milling blank according to the invention or a moulded part produced therefrom for use as an indirect dental restoration, comprising the following steps:

(i) production or provision of a milling blank containing water in an amount of less than 25% of the water sorption $W_{sp}$, preferably less than 15% and particularly preferably less than 10%, (ii) adjustment of the conditions in which the milling blank provided or produced in step (i) sorbs water and maintenance of these conditions until the milling blank contains water in an amount of at least 25% of the water sorption $W_{sp}$, and preferably water-tight sealing or enclosing of the milling blank produced.

A method for producing a moulded part according to the invention for use as an indirect dental restoration preferably comprises the following additional step:

(iii) milling of the moulded part from the milling blank produced in step (ii), preferably by means of a CAD/CAM milling device, and preferably polishing of the moulded part.

A method for producing a milling blank according to the invention preferably comprises an additional step in which the milling blank is sealed or enclosed in a water-tight manner, preferably enclosed in a water-tight manner by a water-tight container, preferably a water-tight blister and/or a water-tight lacquer and/or a water-tight wax sheath. The above explanations of the term "water-tight" and corresponding preferred configurations apply correspondingly.

After an indirect dental restoration, for example a crown, has been milled by the CAD/CAM—method from a milling blank according to the invention and a tooth stump has been prepared, a dentist will ordinarily roughen the inner surface of the prepared indirect dental restoration, for example the crown, by means of sandblasting, then clean and prime it. The bonding is then applied to the core and cured, a luting cement is finally applied to the indirect dental restoration (for example, filled into the crown) and the indirect dental restoration is then bonded to the tooth stump (e.g., the crown is placed on the tooth stump).

The present invention also relates to use of the water sorption method for adjusting the degree of swelling of a milling blank before milling in order to produce a dental moulded part for use as an indirect dental restoration.

The method of selectively adjusting milling blanks by means of water sorption before milling to a specified degree of swelling (and a corresponding capacity for further swelling) in order in this manner to carry out milling into corresponding dental moulded parts that can be particularly favorably used as indirect dental restorations is not known from the prior art. It is not known from the prior art that such a method advantageously imparts to the resulting dental moulded part a particularly high degree of retention. With respect to preferred configurations of the use according to the invention, reference is made to all of the above explanations, which apply mutatis mutandis.

The present invention also relates to a kit for producing indirect dental restorations, comprising:
two or more milling blanks of different colours
and
one or a plurality of dental compositions for bonding a moulded part milled from one of the milling blanks to a dental object in the oral cavity, preferably selected from the group consisting of primers, adhesives and luting cements,
and preferably
further accessories such as brushes, polishing agents and mixing tips.

The present invention also relates to a therapeutic or cosmetic method for indirect dental restoration, comprising the following steps:

i) production or provision of a milling blank, preferably according to the invention (as defined above and in the claim, more particularly as referred to above as preferred) containing water in an amount of less than 25% of the water sorption $W_{SP}$, preferably less than 15%, and particularly preferably less than 10%, ii) adjustment of the conditions in which the milling blank provided or produced in step (i) sorbs water and maintenance of these conditions until the milling blank contains water in an amount of at least 25%, preferably at least 50%, more preferably at least 75%, and particularly preferably at least 90% of the water sorption $W_{SP}$, and optionally watertight sealing or enclosing of the milling blank produced (preferably according to the invention), wherein the conditions are preferably maintained until the difference between the water sorption $W_{SP}$ and the water content of the milling blank is less than 10 μg/mm³, preferably less than 8 μg/mm³, and preferably less than 4 μg/mm³, iii) milling of a moulded part for use as an indirect dental restoration from the milling blank produced in step (ii), and optionally, polishing of the moulded part, wherein the milling is carried out by means of a CAD/CAM milling device based on three-dimensional geometric data of the restoration, and (iv) bonding of the moulded part produced in step (iii) to a dental object in the oral cavity.

REFERENCES TO DOCUMENTS

[1] Roggendorf M J, Kunzi B, Ebert J, Roggendorf H C, Frankenberger R, Reich S M; Sevenyear clinical performance of CEREC-2 all-ceramic CAD/CAM restorations placed within deeply destroyed teeth. Clin Oral Investig 2012, 16(5), 1413-1424.

[2] Frankenberger R, Petschelt A, Kramer N; Leucite-reinforced glass ceramic inlays and onlays after six years: clinical behavior. Oper Dent 2000, 25(6), 459-465.

[3] Frankenberger R, Taschner M, Garcia-Godoy F, Petschelt A, Kramer N; Leucite-reinforced glass ceramic inlays and onlays after 12 years. Adhes Dent 2008, 10(5), 393-398.

[4] Otto T, De Nisco S; Computer-aided direct ceramic restorations: a 10-year prospective clinical study of Cerec CAD/CAM inlays and onlays. Int J Prosthodont 2002, 15(2), 122-128.

[5] Posselt A, Kerschbaum T; Longevity of 2328 chairside Cerec inlays and onlays. Int J Comput Dent 2003, 6(3), 231-248.

[6] Otto T, Schneider D; Long-term clinical results of chairside Cerec CAD/CAM inlays and onlays: a case series. Int J Prosthodont 2008, 21(1), 53-59.

[7] Reiss B; Clinical results of CEREC inlays in a dental practice over a period of 18 years. Int J Comput Dent 2006, 9(1), 11-22.

[8] Kassem A S, Atta O, El-Mowafy O; Combined effects of thermocycling and load-cycling on microleakage of computer-aided design/computer-assisted manufacture molar crowns. Int J Prosthodont 2011, 24(4), 376-378.

[9] Kassem A S, Atta O, El-Mowafy O; Fatigue resistance and microleakage of CAD/CAM ceramic and composite molar crowns. J Prosthodont 2012, 21(1), 28-32.

[10] Attia A, Abdelaziz K M, Freitag S, Kern M; Fracture load of composite resin and feldspathic all-ceramic CAD/CAM crowns. J Prosthet Dent 2006, 95(2), 117-123.

[11] Ramirez-Sebastia A, Bortolotto T, Roig M, Krejci I; Composite vs Ceramic Computer-aided Design/Computer-assisted Manufacturing Crowns in Endodontically Treated Teeth: Analysis of Marginal Adaptation. Oper Dent 2013, 38(6), 663-673.

[12] Lauvahutanon S, Takahashi H, Shiozawa M, Iwasaki N, Asakawa Y, Oki M, Finger W J, Arksornnukit M; Mechanical properties of composite resin blocks for CAD/CAM. Dent Mater J 2014, 33(5), 705-710.

[13] Heintze S D; Crown pull-off test (crown retention test) to evaluate the bonding effectiveness of luting agents. Dental Materials 2010, 36(3), 193-206.

[14] Bahr N, Keul C, Edelhoff D, Eichberger M, Roos M, Gernet W, Stawarczyk B; Effect of different adhesives combined with two resin composite cements on shear bond strength to polymeric CAD/CAM materials. Dent Mater J 2013, 32(3), 492-501.

[15] Güngör M B, Nemli S K, Bal B T, Ünyer S, Dogan A; Effect of surface treatments on shear bond strength of resin composite bonded to CAD/CAM resin-ceramic hybrid materials. Adv Prosthodont 2016, 8, 259-266.

[16] Elsaka S E; Bond strength of novel CAD/CAM restorative materials to self-adhesive resin cement: the effect of surface treatments. Adhes Dent 2014, 16(6), 531-540.

[17] Yoshida K, Kamada K, Atsuta M; Effects of two silane coupling agents, a bonding agent, and thermal cycling on the bond strength of a CAD/CAM composite material cemented with two resin luting agents. J Prosthet Dent 2001, 85(2), 184-189.

[18] Keul C, Müller-Hahl M, Eichberger M, Liebermann A, Roos M, Edelhoff D, Stawarczyk B; Impact of different adhesives on work of adhesion between CAD/CAM polymers and resin composite cements. J Dent 2014, 42(9), 1105-1114.

[19] Stawarczyk B, Basler T, Ender A, Roos M, Ozcan M, Hammerle C; Effect of surface conditioning with airborne-particle abrasion on the tensile strength of polymeric CAD/CAM crowns luted with self-adhesive and conventional resin cements. J Prosthet Dent 2012, 107(2), 94-101.

[20] Gilbert S; Effect of the test method on bonding between CAD/CAM high-performance polymers and resin-based bonding materials after different pretreatments. Dissertation, Ludwig Maximilian University of Munich 2014.

[21] Martin A; Tensile bond strength tests and high-performance resins after different pretreatment methods. Dissertation, Ludwig Maximilian University of Munich 2015.

[22] Stawarczyk B, Stich N, Eichberger M, Edelhoff D, Roos M, Gernet W, Keul C; Longterm tensile bond strength of differently cemented nanocomposite CAD/CAM crowns on dentin abutment. Dental Materials 2014, 30(3), 334-342.

[23] Basler T; Effect of surface conditioning with air-abrasion on the tensile strength of polymeric CAD/CAM crowns luted with self-adhesive and conventional resin cements. Dissertation, University of Zurich 2011

[24] Frankenberger R, Hartmann V E, Krech M, Kramer N, Reich S, Braun A, Roggendorf M; Adhesive bonding of new CAD/CAM-materials. Int J Comput Dent 2015, 18(1), 9-20.

[25] Shetty R, Shenoy K, Dandekeri S, Suhaim K S, Ragher M, Francis J; Resin-Matrix Ceramics—An Overview. International Journal of Recent Scientific Research 2015, 6(11), 7414-7417.

[26] Vanoorbeek S, Vandamme K, Lijnen I, Naert I; Computer-aided designed/computer-assisted manufactured composite resin versus ceramic single-tooth restorations: a 3-year clinical study. Int J Prosthodont. 2010, 23(3), 223-230.

[27] Schepke U, Meijer H J A, Vermeulen K M, Raghoebar G M, Cune M S; Clinical Bonding of Resin Nano Ceramic Restorations to Zirconia Abutments: A Case Series within a Randomized Clinical trial. Clin Implant Dent Relat Res 2016, 18(5), 984-992.

EXAMPLES

Abbreviations

Bis-EMA2,6: Ethoxylated bisphenol A dimethacrylate with an average of 2.6 ethylene oxide units Bis-EMA4: Ethoxylated bisphenol A dimethacrylate with an average of 4 ethylene oxide units Bis-EMA6: Ethoxylated bisphenol A dimethacrylate with an average of 6 ethylene oxide units Bis-EMA10: Ethoxylated bisphenol A dimethacrylate with an average of 10 ethylene oxide units TCDDMA: Bis(methacryloyloxymethyl)tricyclo[5.2.1.0$^{2,6}$]decane UDMA: 7,7,9-trimethyl-4,13-dioxo-3,14-dioxa-5,12-diazahexadecane-1,16-dioxydimethacrylate TEGDMA: Triethylene glycol methacrylate HDDMA: 1,6-Hexanediol dimethacrylate DODMA: 1,12-Dodecanediol dimethacrylate Dental glass 1: Barium aluminum borosilicate glass (D50 0.8 μm/D25 0.5 μm/D75 1.0 μm), silanised Dental glass 2: Barium aluminum borosilicate glass (D50 2.7 μm/D25 1.4 μm/D75 6.1 μm), silanised Dental glass 3: Barium aluminum borosilicate glass (D50 1.1 μm/D25 0.7 μm/D75 1.4 μm), silanised Dental glass 4: Barium aluminum borosilicate glass (D50 1.4 μm/D25 1.1 μm/D75 2.1 μm), silanised Dental glass 5: Barium aluminum borosilicate glass (D50 1.4 μm/D25 0.8 μm/D75 2.9 μm), silanised Nano-SiO2: Non-agglomerated, non-aggregated silica (D50 40 nm), silanised BPO: Dibenzoyl peroxide Production of the Composite Pastes:

The individual components were weighed in the proportions given in Tables 2 to 14, homogenised for 30 min at 50 rpm on a laboratory kneader (PC Laboratory System, Magden CH) and then deaerated on the laboratory kneader for 15 min at 50 rpm and −0.85 bar.

Production of the Composite Blocks:

For production of the composite blocks, the individual pastes were poured into moulds (15 mm×15 mm×20 mm). Curing was carried out isostatically at 250 bar with the following temperature program (20° C.—2° C./min—120° C. (30 min)—5° C./min—20° C.).

Biaxial flexural strength (BFS): Biaxial flexural strength was determined analogously to DIN EN ISO 6872:2009 (7.3.3). For this purpose, cylinders with a diameter of 14 mm were first milled from the composite blocks in a 5-axis milling machine (250i, imes-icore GmbH). Using a high-speed saw (IsoMet 4000, Buehler), plates with a thickness of 1.2 mm were then produced from these cylinders, deburred, ground, and polished. The samples were loaded to failure at a transverse speed of 1 mm/min, and the biaxial flexural strength was calculated according to the formula given under 7.3.3.4. A value of 0.25 was used as Poisson's ratio.

3-point flexural strength (3PFS): Flexural strength was determined analogously to DIN EN ISO 6872:2009 (7.3.2) with a span distance of 12 mm and a contact roll diameter of 2 mm. For this purpose, sample specimens with a width of 4 mm, a thickness of 1.2 mm and a length of 18 mm were produced from the composite blocks using a high-speed saw (IsoMet 4000, Buehler), deburred, ground, and polished. The samples were loaded to failure at a transverse speed of 1 mm/min, and the 3-point flexural strength was calculated according to the formula given under 7.3.2.4.1.

Elastic modulus (E): The elastic modulus was determined analogously to the calculation in ADA Specification No. 27—1993 (7.8.4.2) as a slope of the stress-strain curve of 3-point flexural strength measurement (see above) in the linear-elastic range.

$$E = \frac{3L}{4bh^3} \frac{\Delta F}{\Delta d}$$

L: Span distance
b: Sample width
h: Sample thickness
Δd: Deformation in the linear-elastic range
ΔF: Change in force for deformation Δd Water sorption ($W_{SP}$): Water sorption was determined analogously to EN ISO 4049:2009 (D) (7.12); the determination methods were then combined, and deviations (particularly with respect to sample geometry) from the method according to EN ISO 4049:2009 (D) were indicated.

From the composite blocks produced, sample specimens with a length of 14.7 mm, a width of 14.7 mm and a thickness of 0.5 mm were produced with a high-speed saw (IsoMet 4000, Buehler), deburred, ground, and polished. The sample specimens (analogously to 7.12.3.1) were dried in the desiccator at 37° C. to constant mass, the mass ($m_1$) was precisely determined to 0.1 mg, and (analogously to 7.12.3.2) the length, the width and the thickness were precisely determined to 0.01 mm; the volume V in mm$^3$ was determined from this. After this, the test specimens (analogously to 7.12.3.3) were stored for 7 days at 37° C. in water. After 7 days, the test specimens were removed, rinsed with water, blotted, moved back and forth in the air for 15 sec and precisely weighed to 0.1 mg 1 min after removal from the water ($m_2$). After this weighing (analogously to 7.12.3.4), the test specimens were dried in the desiccator at 37° C. to constant mass, and the mass ($m_3$) was determined to 0.1 mg. The water sorption was calculated according to Equation (2) given under 7.12.4.1.

Water treatment/conditioning of the composite blocks and determination of the degree of conditioning: Produced composite blocks were dried in the desiccator at 37° C. to constant mass, the mass of the composite blocks dried in this matter ($m_0$) was precisely determined to 0.1 mg, and the length, width and thickness were precisely determined to 0.01 mm; the volume V in mm$^3$ was determined from this. After this, the composite blocks were stored in water for 1 week at 60° C. After 1 week, the composite blocks were removed, rinsed with water, blotted, moved back and forth in the air for 15 sec and precisely weighed to 0.1 mg 1 min after removal from the water ($m_{1\ week}$). The composite blocks were then again stored at 60° C. in water. At weekly intervals, the composite blocks were again removed, rinsed with water, blotted, moved back and forth in the air for 15 sec and precisely weighed to 0.1 mg 1 min after removal from the water ($m_{2\ weeks}$, $m_{3\ weeks}$, etc.). The degree of conditioning was determined for the respective times in relation to the water sorption determined on 0.5 mm thick plates of the same composition ($W_{SP}$) (see above) according to the following formula.

$$\text{Degree of conditioning}_{n\ weeks}[\%] = \frac{m_{n\ weeks} - m_0}{V_{composite\ block} \times W_{SP}} \times 100\%$$

Similarly, the degree of conditioning was also determined at a storage temperature of 37° C. (Note: because of their dimensions, the composite blocks reach their full degree of water saturation more slowly than the 0.5 mm thick plates used for determination of the water sorption.)

Figure 2:
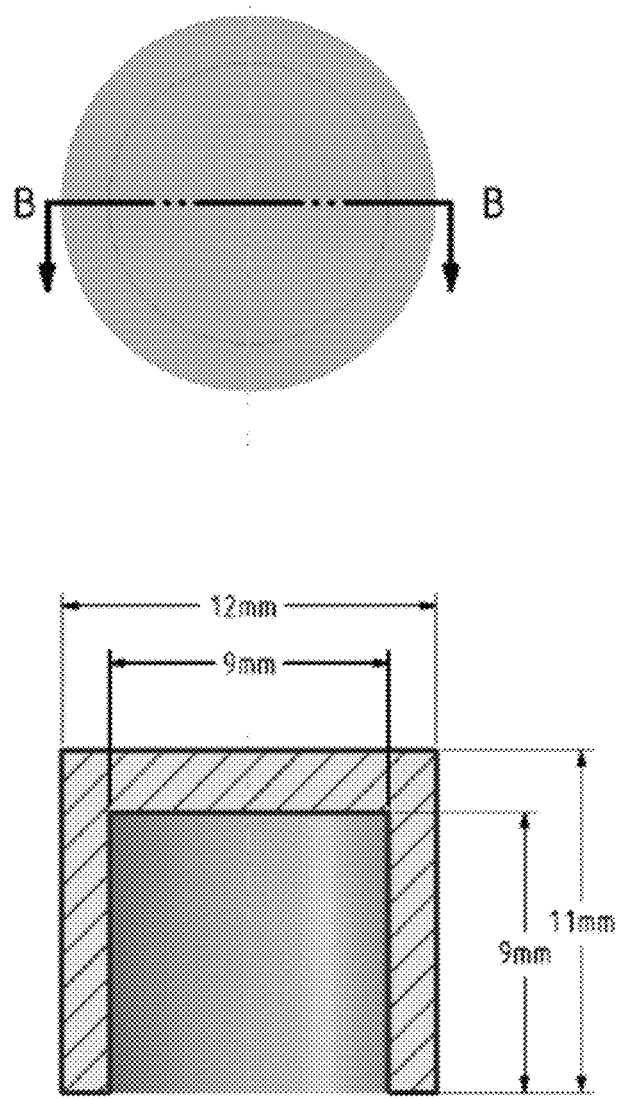
FIG. 2 shows a top view and a cross sectional view of an idealised crowns having the form of a hollow cylinders closed on one side and open on the other.

Linear swelling (LS): In 5-axis milling machine (250i, imes-icore GmbH), idealised crowns were produced from the composite blocks as sample specimens. These idealised crowns are hollow cylinders closed on one side (cf. FIG. 2).

The height is 11 mm, the outer diameter 12 mm and the inner diameter 9 mm. This corresponds to a wall thickness of 1.5 mm. The thickness of the cover plate is 2 mm. After this, the idealised crowns were deburred, ground, and polished. The resulting sample specimens were dried in the desiccator at 37° C. to constant mass, and the inner diameter of the dried sample specimens at the cylinder base at two sites orthogonal to each other was precisely determined to 0.001 mm ($L_1$ and $L_2$). After this, the test specimens were stored in water for 7 days (1 week) at 37° C. After 7 days, the test specimens were removed, rinsed with water, blotted, and moved back and forth in the air for 15 sec; 1 min after removal from the water, the inner diameter at the cylinder base at the same two sites as before was precisely determined to 0.001 mm ($L_3$ and $L_4$). After measurement, the test specimens were stored in water for a further 7 days (1 week) at 37° C. (total: 2 weeks). After this, the test specimens were removed and dried as described above, and the inner diameter at the same sites was again precisely determined to 0.001 mm ($L_5$ and $L_6$). After measurement, the test specimens were stored in water for a further 14 days (2 weeks) at 37° C. (total: 4 weeks). The test specimens were then removed and dried as described above, and the inner diameter at the same sites was again precisely determined to 0.001 mm ($L_7$ and $L_8$). After measurement, the test specimens were stored in water for a further 28 days (4 weeks) at 37° C. (total: 8 weeks). The test specimens were then removed and dried as described above, and the inner diameter at the same sites was again precisely determined to 0.001 mm ($L_9$ and $L_{10}$). The linear swelling in % at the respective measurement times can be determined according to the following formulae.

$$LS_{1week}[\%] = \frac{\frac{L_3+L_4}{2} - \frac{L_1+L_2}{2}}{\frac{L_1+L_2}{2}} \times 100\%$$

$$LS_{2weeks}[\%] = \frac{\frac{L_5+L_6}{2} - \frac{L_1+L_2}{2}}{\frac{L_1+L_2}{2}} \times 100\%$$

$$LS_{4weeks}[\%] = \frac{\frac{L_7+L_8}{2} - \frac{L_1+L_2}{2}}{\frac{L_1+L_2}{2}} \times 100\%$$

$$LS_{8weeks}[\%] = \frac{\frac{L_9+L_{10}}{2} - \frac{L_1+L_2}{2}}{\frac{L_1+L_2}{2}} \times 100\%$$

Residue on ignition: In order to determine residue on ignition, crucibles were heated for 10 hr to 150° C., allowed to cool in the desiccator to room temperature and then precisely weighed to 0.1 mg ($m_1$). Approx. 1 g of the respective composite block was crushed, ground and precisely weighed into the crucible to 0.1 mg ($m_2$). Heating was carried out for 3 hr in a muffle furnace to 575° C., the crucible was then allowed to cool to room temperature in the desiccator and the mass (crucible with residue) was then precisely determined to 0.1 mg ($m_3$). The residue on ignition was calculated according to the following formula.

$$\text{Residue on ignition}[\%] = \frac{m_3 - m_1}{m_2} \times 100\%$$

Adhesion: Zirconium dioxide abutments were produced as idealised cones. The zirconium dioxide abutments were configured as truncated cones having a diameter of 10.0 mm at the end surface, an angle of 5° and a height of 15 mm. In a 5-axis milling machine (250i, imes-icore GmbH), idealised crowns were produced from the composite blocks in the shape of caps as sample specimens (see below for degree of conditioning). The inner surface of the crowns corresponded to the outer surface of the zirconium dioxide abutments, with a gap of 70 µm (for the sorption of bonding agents) being included in calculation. Accordingly, the inner diameter at the end surface was 10.14 mm. The angle correspondingly was also 5° and the inner height was 6.55 mm. The overall wall thickness was 1.5 mm. Ceramic crowns having the same dimensions (IPS e.max CAD, Ivoclar Vivadent) were produced as a comparison.

The inner crown surface was sandblasted with aluminum dioxide (50 µm) (1.5 bar). After this, a bonding agent (Ceramic Bond, VOCO GmbH) was applied to the zirconium dioxide abutment and inner crown surface and allowed to dry for 60 sec. The crowns were then bonded to the abutments using a composite-based bonding system (Bifix QM, VOCO GmbH). Curing was carried out for 24 hr at 37° C. Adhesion tests were then carried out as pull-off tests on a universal testing machine at a test speed of 1 mm/min in the following four groups.

a) The crowns were produced from unconditioned blocks, and the adhesion test was carried out immediately after curing.

b) The crowns were produced from unconditioned blocks, and the adhesion test was carried out after curing and storage in water for 8 weeks at 37° C.

c) The crowns were produced from conditioned blocks (storage in water at 60° C. until a degree of conditioning of at least 90% was reached in the weekly test), and the adhesion test was carried out immediately after curing.

d) The crowns were produced from conditioned blocks (storage in water at 60° C. until a degree of conditioning of at least 90% was reached in the weekly test), and the adhesion test was carried out after curing and storage in water for 8 weeks at 37° C.

Particle Size Determination:

Particle size determination of Nano-SiO2 nanoparticles was carried out by dynamic light scattering (DLS) with a Zetasizer Nano ZS (Malvern) at 0.5 wt. % in 2-butanone (volume weighting).

Particle size determination of the microparticles (dental glass) was carried out by means of laser diffraction using a Beckmann Coulter LS 13320.

TABLE 1

| | References | | | |
|---|---|---|---|---|
| | Lava Ultimate (3M Espe) | Cerasmart (GC) | Block HC (Shofu) | Crios (Coltene) |
| Filler content (manufacturer data) [%] | 80 | | | 70.7 |
| Residue on ignition [%] | 73 | 65 | 62 | 70 |
| Biaxial flexural strength [MPa] | 174 | 214 | 147 | 232 |
| 3-point flexural strength [MPa] | 163 | 159 | 122 | 198 |

TABLE 1-continued

|  | References | | | |
|---|---|---|---|---|
|  | Lava Ultimate (3M Espe) | Cerasmart (GC) | Block HC (Shofu) | Crios (Coltene) |
| E modulus [GPa] | 11.8 | 9.9 | 8.7 | 12.7 |
| $W_{SP}$ [µg/mm³] | 36 | 29 | 40 | 23 |
| $W_{SP}/E$ [µg/(GPa × mm³)] | 3.05 | 2.93 | 4.60 | 1.81 |
| LS (1 week) [%] | 0.23% | 0.19% | 0.27% | 0.15% |
| LS (2 weeks) [%] | 0.42% | 0.36% | 0.48% | 0.27% |
| LS (4 weeks) [%] | 0.51% | 0.42% | 0.60% | 0.34% |
| LS (8 weeks) [%] | 0.53% | 0.44% | 0.63% | 0.35% |

TABLE 2

|  |  |  | Example | | | |
|---|---|---|---|---|---|---|
|  |  |  | 1 | 2 | 3 | 4 |
| Filler (a) | (a1a) | Dental glass 1 | 13.00 | 13.00 | 13.00 | 13.00 |
|  | (a1b) | Dental glass 2 | 57.50 | 57.50 | 57.50 | 57.50 |
|  |  | Dental glass 3 |  |  |  |  |
|  |  | Dental glass 4 |  |  |  |  |
|  |  | Dental glass 5 |  |  |  |  |
|  | (a2) | Nano-SiO₂ (40 nm) | 15.00 | 15.00 | 15.00 | 15.00 |
|  |  | Total (a) | 85.50 | 85.50 | 85.50 | 85.50 |
| Monomers (b) | (b1a) | Bis-EMA2,6 | 6.00 | 6.00 | 6.00 | 6.50 |
|  |  | Bis-EMA4 |  |  |  |  |
|  | (b1b) | Bis-EMA6 |  |  |  |  |
|  |  | Bis-EMA10 |  |  |  |  |
|  | (b2) | TCDDMA | 3.75 | 5.00 | 2.50 | 3.50 |
|  |  | UDMA | 3.75 | 2.50 | 5.00 | 3.50 |
|  |  | HDDMA | 0.70 | 0.70 | 0.70 | 0.70 |
|  |  | DODMA |  |  |  |  |
|  |  | TEGDMA |  |  |  |  |
|  |  | Total (b) | 14.20 | 14.20 | 14.20 | 14.20 |
| Initiators (c) |  | BPO | 0.30 | 0.30 | 0.30 | 0.30 |
|  |  | Total | 100.00 | 100.00 | 100.00 | 100.00 |

TABLE 3

|  | Example | | | |
|---|---|---|---|---|
|  | 1 | 2 | 3 | 4 |
| (a1a)/(a1b) | 0.23 | 0.23 | 0.23 | 0.23 |
| (a2)/[(a1a) + (a1b)] | 0.21 | 0.21 | 0.21 | 0.21 |
| (b1a)/(b) × 100% | 42.3% | 42.3% | 42.3% | 45.8% |
| Biaxial flexural strength [MPa] | 301 | 269 | 292 | 284 |
| 3-point flexural strength [MPa] | 274 | 241 | 266 | 259 |
| E modulus [GPa] | 18.3 | 15.8 | 18.6 | 16.4 |
| $W_{SP}$ [µg/mm³] | 13 | 11 | 15 | 12 |
| $W_{SP}/E$ [µg/(GPa × mm³)] | 0.71 | 0.70 | 0.81 | 0.73 |
| LS (1 week) [%] | 0.09% | 0.09% | 0.10% | 0.08% |
| LS (2 weeks) [%] | 0.15% | 0.14% | 0.16% | 0.13% |
| LS (4 weeks) [%] | 0.19% | 0.18% | 0.19% | 0.17% |
| LS (8 weeks) [%] | 0.19% | 0.19% | 0.20% | 0.18% |
| Adhesion (group a) [N] | 530 | 526 | 535 | 527 |
| Adhesion (group b) [N] | 411 | 407 | 408 | 407 |
| Adhesion (group c) [N] | 526 | 512 | 518 | 514 |
| Adhesion (group d) [N] | 501 | 493 | 497 | 496 |

TABLE 4

|  |  |  | Example | | | |
|---|---|---|---|---|---|---|
|  |  |  | 5 | 6 | 7 | 8 |
| Filler (a) | (a1a) | Dental glass 1 | 13.00 | 13.00 | 13.00 | 13.00 |
|  | (a1b) | Dental glass 2 | 57.50 | 57.50 | 57.50 | 57.50 |
|  |  | Dental glass 3 |  |  |  |  |
|  |  | Dental glass 4 |  |  |  |  |
|  |  | Dental glass 5 |  |  |  |  |
|  | (a2) | Nano-SiO₂ (40 nm) | 15.00 | 15.00 | 15.00 | 15.00 |
|  |  | Total (a) | 85.50 | 85.50 | 85.50 | 85.50 |
| Monomers (b) | (b1a) | Bis-EMA2,6 | 7.00 | 5.80 | 6.00 | 6.00 |
|  |  | Bis-EMA4 |  |  |  |  |
|  | (b1b) | Bis-EMA6 |  |  |  |  |
|  |  | Bis-EMA10 |  |  |  |  |
|  | (b2) | TCDDMA | 3.25 | 3.85 | 3.75 | 3.75 |
|  |  | UDMA | 3.25 | 3.85 | 3.75 | 3.75 |
|  |  | HDDMA | 0.70 | 0.70 |  |  |
|  |  | DODMA |  |  | 0.70 |  |
|  |  | TEGDMA |  |  |  | 0.70 |
|  |  | Total (b) | 14.20 | 14.20 | 14.20 | 14.20 |
| Initiators (c) |  | BPO | 0.30 | 0.30 | 0.30 | 0.30 |
|  |  | Total | 100.00 | 100.00 | 100.00 | 100.00 |

TABLE 5

|  | Example | | | |
|---|---|---|---|---|
|  | 5 | 6 | 7 | 8 |
| (a1a)/(a1b) | 0.23 | 0.23 | 0.23 | 0.23 |
| (a2)/[(a1a) + (a1b)] | 0.21 | 0.21 | 0.21 | 0.21 |
| (b1a)/(b) × 100% | 49.3% | 40.8% | 42.3% | 42.3% |
| Biaxial flexural strength [MPa] | 271 | 295 | 261 | 299 |
| 3-point flexural strength [MPa] | 251 | 270 | 237 | 271 |
| E modulus [GPa] | 15.1 | 18.7 | 15.1 | 19.1 |
| $W_{SP}$ [µg/mm³] | 13 | 15 | 11 | 14 |
| $W_{SP}/E$ [µg/(GPa × mm³)] | 0.86 | 0.80 | 0.73 | 0.73 |
| LS (1 week) [%] | 0.09% | 0.09% | 0.05% | 0.07% |
| LS (2 weeks) [%] | 0.18% | 0.17% | 0.11% | 0.13% |
| LS (4 weeks) [%] | 0.21% | 0.20% | 0.17% | 0.16% |
| LS (8 weeks) [%] | 0.22% | 0.21% | 0.19% | 0.17% |
| Adhesion (group a) [N] | 510 | 523 | 504 | 529 |
| Adhesion (group b) [N] | 403 | 410 | 417 | 409 |
| Adhesion (group c) [N] | 501 | 513 | 498 | 510 |
| Adhesion (group d) [N] | 491 | 502 | 490 | 495 |

TABLE 6

|  |  |  | Example | | | |
|---|---|---|---|---|---|---|
|  |  |  | 9 | 10 | 11 | 12 |
| Filler (a) | (a1a) | Dental glass 1 |  | 13.00 | 13.00 | 13.00 |
|  | (a1b) | Dental glass 2 | 70.50 | 57.50 | 57.50 | 57.50 |
|  |  | Dental glass 3 |  |  |  |  |
|  |  | Dental glass 4 |  |  |  |  |
|  |  | Dental glass 5 |  |  |  |  |
|  | (a2) | Nano-SiO₂ (40 nm) | 15.00 | 15.00 | 15.00 | 15.00 |
|  |  | Total (a) | 85.50 | 85.50 | 85.50 | 85.50 |

TABLE 6-continued

|  |  |  | Example | | | |
|---|---|---|---|---|---|---|
|  |  |  | 9 | 10 | 11 | 12 |
| Monomers (b) | (b1a) | Bis-EMA2,6 | 6.00 |  |  |  |
|  |  | Bis-EMA4 |  | 6.00 |  |  |
|  | (b1b) | Bis-EMA6 |  |  | 6.00 |  |
|  |  | Bis-EMA10 |  |  |  | 6.00 |
|  | (b2) | TCDDMA | 3.75 | 3.75 | 3.75 | 3.75 |
|  |  | UDMA | 3.75 | 3.75 | 3.75 | 3.75 |
|  |  | HDDMA | 0.70 | 0.70 | 0.70 | 0.70 |
|  |  | DODMA |  |  |  |  |
|  |  | TEGDMA |  |  |  |  |
|  | Total (b) |  | 14.20 | 14.20 | 14.20 | 14.20 |
| Initiators (c) |  | BPO | 0.30 | 0.30 | 0.30 | 0.30 |
|  | Total |  | 100.00 | 100.00 | 100.00 | 100.00 |

TABLE 7

|  | Example | | | |
|---|---|---|---|---|
|  | 9 | 10 | 11 | 12 |
| (a1a)/(a1b) | 0.00 | 0.23 | 0.23 | 0.23 |
| (a2)/[(a1a) + (a1b)] | 0.21 | 0.21 | 0.21 | 0.21 |
| (b1a)/(b) × 100% | 42.3% | 42.3% | 0.0% | 0.0% |
| Biaxial flexural strength [MPa] | 256 | 289 | 262 | 219 |
| 3-point flexural strength [MPa] | 221 | 262 | 239 | 198 |
| E modulus [GPa] | 13.4 | 17.7 | 13.7 | 12.6 |
| $W_{SP}$ [μg/mm³] | 18 | 15 | 19 | 26 |
| $W_{SP}$/E [μg/(GPa × mm³)] | 1.34 | 0.85 | 1.39 | 2.06 |
| LS (1 week) [%] | 0.13% | 0.10% | 0.15% | 0.17% |
| LS (2 weeks) [%] | 0.22% | 0.16% | 0.27% | 0.29% |
| LS (4 weeks) [%] | 0.28% | 0.21% | 0.31% | 0.36% |
| LS (8 weeks) [%] | 0.28% | 0.22% | 0.32% | 0.38% |
| Adhesion (group a) [N] | 511 | 513 | 509 | 508 |
| Adhesion (group b) [N] | 377 | 398 | 299 | 87 |
| Adhesion (group c) [N] | 497 | 502 | 493 | 478 |
| Adhesion (group d) [N] | 472 | 488 | 451 | 412 |

TABLE 8

|  |  |  | Example | | | |
|---|---|---|---|---|---|---|
|  |  |  | 13 | 14 | 15 | 16 |
| Filler (a) | (a1a) | Dental glass 1 | 12.70 | 12.40 | 13.00 | 12.40 |
|  | (a1b) | Dental glass 2 | 56.10 | 54.70 | 57.50 | 54.70 |
|  |  | Dental glass 3 |  |  |  |  |
|  |  | Dental glass 4 |  |  |  |  |
|  |  | Dental glass 5 |  |  |  |  |
|  | (a2) | Nano-SiO$_2$ (40 nm) | 14.60 | 14.20 | 15.00 | 14.20 |
|  | Total (a) |  | 83.40 | 81.30 | 85.50 | 81.30 |
| Monomers (b) | (b1a) | Bis-EMA2,6 | 6.90 | 7.80 | 5.00 | 6.40 |
|  |  | Bis-EMA4 |  |  |  |  |
|  | (b1b) | Bis-EMA6 |  |  |  |  |
|  |  | Bis-EMA10 |  |  |  |  |
|  | (b2) | TCDDMA | 4.30 | 4.85 | 3.75 | 6.00 |
|  |  | UDMA | 4.30 | 4.85 | 3.75 | 6.00 |
|  |  | HDDMA | 0.80 | 0.90 | 1.70 |  |
|  |  | DODMA |  |  |  |  |
|  |  | TEGDMA |  |  |  |  |
|  | Total (b) |  | 16.30 | 18.40 | 14.20 | 18.40 |
| Initiators (c) |  | BPO | 0.30 | 0.30 | 0.30 | 0.30 |
|  | Total |  | 100.00 | 100.00 | 100.00 | 100.00 |

TABLE 9

|  | Example | | | |
|---|---|---|---|---|
|  | 13 | 14 | 15 | 16 |
| (a1a)/(a1b) | 0.23 | 0.23 | 0.23 | 0.23 |
| (a2)/[(a1a) + (a1b)] | 0.21 | 0.21 | 0.21 | 0.21 |
| (b1a)/(b) × 100% | 42.3% | 42.4% | 35.2% | 34.8% |
| Biaxial flexural strength [MPa] | 266 | 201 | 189 | 203 |
| 3-point flexural strength [MPa] | 240 | 175 | 169 | 177 |
| E modulus [GPa] | 16.7 | 13.7 | 11.8 | 12.1 |
| $W_{SP}$ [μg/mm³] | 15 | 19 | 16 | 17 |
| $W_{SP}$/E [μg/(GPa × mm³)] | 0.90 | 1.39 | 1.36 | 1.40 |
| LS (1 week) [%] | 0.10% | 0.16% | 0.14% | 0.14% |
| LS (2 weeks) [%] | 0.17% | 0.26% | 0.24% | 0.26% |
| LS (4 weeks) [%] | 0.23% | 0.31% | 0.32% | 0.31% |
| LS (8 weeks) [%] | 0.23% | 0.31% | 0.32% | 0.32% |
| Adhesion (group a) [N] | 514 | 507 | 500 | 502 |
| Adhesion (group b) [N] | 379 | 274 | 281 | 277 |
| Adhesion (group c) [N] | 497 | 483 | 485 | 488 |
| Adhesion (group d) [N] | 485 | 443 | 456 | 440 |

TABLE 10

|  |  |  | Example | | | |
|---|---|---|---|---|---|---|
|  |  |  | 17 | 18 | 19 | 20 |
| Filler (a) | (a1a) | Dental glass 1 | 13.00 | 12.40 | 12.70 | 12.70 |
|  | (a1b) | Dental glass 2 | 57.50 |  |  |  |
|  |  | Dental glass 3 |  | 54.70 |  |  |
|  |  | Dental glass 4 |  |  | 56.10 |  |
|  |  | Dental glass 5 |  |  |  | 56.10 |
|  | (a2) | Nano-SiO$_2$ (40 nm) | 15.00 | 14.20 | 14.60 | 14.60 |
|  | Total (a) |  | 85.50 | 81.30 | 83.40 | 83.40 |
| Monomers (b) | (b1a) | Bis-EMA2,6 | 7.50 | 7.80 | 6.90 | 6.90 |
|  |  | Bis-EMA4 |  |  |  |  |
|  | (b1b) | Bis-EMA6 |  |  |  |  |
|  |  | Bis-EMA10 |  |  |  |  |
|  | (b2) | TCDDMA | 3.00 | 4.85 | 4.30 | 4.30 |
|  |  | UDMA | 3.00 | 4.85 | 4.30 | 4.30 |
|  |  | HDDMA | 0.70 | 0.90 | 0.80 | 0.80 |
|  |  | DODMA |  |  |  |  |
|  |  | TEGDMA |  |  |  |  |
|  | Total (b) |  | 14.20 | 18.40 | 16.30 | 16.30 |
| Initiators (c) |  | BPO | 0.30 | 0.30 | 0.30 | 0.30 |
|  | Total |  | 100.00 | 100.00 | 100.00 | 100.00 |

TABLE 11

| | Example 17 | Example 18 | Example 19 | Example 20 |
|---|---|---|---|---|
| (a1a)/(a1b) | 0.23 | 0.23 | 0.23 | 0.23 |
| (a2)/[(a1a) + (a1b)] | 0.21 | 0.21 | 0.21 | 0.21 |
| (b1a)/(b) × 100% | 52.8% | 42.4% | 42.3% | 42.3% |
| Biaxial flexural strength [MPa] | 198 | 213 | 265 | 231 |
| 3-point flexural strength [MPa] | 177 | 194 | 242 | 211 |
| E modulus [GPa] | 11.0 | 14.4 | 14.7 | 12.5 |
| $W_{SP}$ [µg/mm$^3$] | 15 | 20 | 16 | 17 |
| $W_{SP}/E$ [µg/(GPa × mm$^3$)] | 1.36 | 1.39 | 1.09 | 1.36 |
| LS (1 week) [%] | 0.16% | 0.18% | 0.12% | 0.14% |
| LS (2 weeks) [%] | 0.25% | 0.27% | 0.19% | 0.23% |
| LS (4 weeks) [%] | 0.30% | 0.31% | 0.25% | 0.30% |
| LS (8 weeks) [%] | 0.31% | 0.31% | 0.26% | 0.31% |
| Adhesion (group a) [N] | 503 | 502 | 506 | 500 |
| Adhesion (group b) [N] | 283 | 271 | 337 | 274 |
| Adhesion (group c) [N] | 493 | 498 | 495 | 493 |
| Adhesion (group d) [N] | 447 | 423 | 472 | 439 |

TABLE 12

| | | | Example 21 | Example 22 | Example 23 | Example 24 |
|---|---|---|---|---|---|---|
| Filler (a) | (a1a) | Dental glass 1 | 35.25 | 7.00 | 10.00 | 13.92 |
| | (a1b) | Dental glass 2 | 35.25 | 60.10 | 44.20 | 61.58 |
| | | Dental glass 3 | | | | |
| | | Dental glass 4 | | | | |
| | | Dental glass 5 | | | | |
| | (a2) | Nano-SiO$_2$ (40 nm) | 15.00 | 14.20 | 25.00 | 10.00 |
| | Total (a) | | 85.50 | 81.30 | 79.20 | 85.50 |
| Monomers (b) | (b1a) | Bis-EMA2,6 | 6.00 | 7.80 | 8.70 | 6.00 |
| | | Bis-EMA4 | | | | |
| | (b1b) | Bis-EMA6 | | | | |
| | | Bis-EMA10 | | | | |
| | (b2) | TCDDMA | 3.75 | 4.85 | 5.40 | 3.75 |
| | | UDMA | 3.75 | 4.85 | 5.40 | 3.75 |
| | | HDDMA | 0.70 | 0.90 | 1.00 | 0.70 |
| | | DODMA | | | | |
| | | TEGDMA | | | | |
| | Total (b) | | 14.20 | 18.40 | 20.50 | 14.20 |
| Initiators (c) | | BPO | 0.30 | 0.30 | 0.30 | 0.30 |
| | Total | | 100.00 | 100.00 | 100.00 | 100.00 |

TABLE 13

| | Example 21 | Example 22 | Example 23 | Example 24 |
|---|---|---|---|---|
| (a1a)/(a1b) | 1.00 | 0.12 | 0.23 | 0.23 |
| (a2)/[(a1a) + (a1b)] | 0.21 | 0.21 | 0.46 | 0.13 |
| (b1a)/(b) × 100% | 42.3% | 42.4% | 42.4% | 42.3% |
| Biaxial flexural strength [MPa] | 204 | 197 | 156 | 188 |
| 3-point flexural strength [MPa] | 181 | 174 | 128 | 145 |
| E modulus [GPa] | 11.7 | 14.3 | 11.7 | 12.4 |
| $W_{SP}$ [µg/mm$^3$] | 19 | 21 | 31 | 21 |
| $W_{SP}/E$ [µg/(GPa × mm$^3$)] | 1.62 | 1.47 | 2.65 | 1.69 |
| LS (1 week) [%] | 0.19% | 0.20% | 0.23% | 0.21% |
| LS (2 weeks) [%] | 0.27% | 0.26% | 0.37% | 0.29% |
| LS (4 weeks) [%] | 0.32% | 0.31% | 0.43% | 0.34% |
| LS (8 weeks) [%] | 0.33% | 0.32% | 0.45% | 0.35% |
| Adhesion (group a) [N] | 504 | 513 | 503 | 505 |
| Adhesion (group b) [N] | 188 | 204 | 53 | 127 |
| Adhesion (group c) [N] | 481 | 488 | 473 | 484 |
| Adhesion (group d) [N] | 421 | 438 | 382 | 417 |

TABLE 14

| | | | Example 25 | Example 26 |
|---|---|---|---|---|
| Filler (a) | (a1a) | Dental glass 1 | 15.00 | 13.50 |
| | (a1b) | Dental glass 2 | 39.50 | 35.50 |
| | | Dental glass 3 | | |
| | | Dental glass 4 | | |
| | | Dental glass 5 | | |
| | (a2) | Nano-SiO$_2$ (40 nm) | 17.00 | 15.35 |
| | Total (a) | | 71.50 | 64.35 |
| Monomers (b) | (b1a) | Bis-EMA2,6 | 12.20 | 15.25 |
| | | Bis-EMA4 | | |
| | (b1b) | Bis-EMA6 | | |
| | | Bis-EMA10 | | |
| | (b2) | TCDDMA | 8.00 | 10.00 |
| | | UDMA | 8.00 | 10.00 |
| | | HDDMA | | |
| | | DODMA | | |
| | | TEGDMA | | |
| | Total (b) | | 28.20 | 35.25 |
| Initiators (c) | | BPO | 0.30 | 0.30 |
| | Total | | 100.00 | 100.00 |

TABLE 15

| | Example 25 | Example 26 | ceramic (comparison) |
|---|---|---|---|
| (a1a)/(a1b) | 0.38 | 0.38 | n.a. |
| (a2)/[(a1a) + (a1b)] | 0.31 | 0.31 | n.a. |
| (b1a)/(b) × 100% | 43.3% | 43.3% | n.a. |
| Biaxial flexural strength [MPa] | 220 | 150 | 360 |
| 3-point flexural strength [MPa] | 201 | 129 | |
| E modulus [GPa] | 11.1 | 8.7 | 95 |
| $W_{SP}$ [µg/mm$^3$] | 20 | 41 | |
| $W_{SP}/E$ [µg/(GPa × mm$^3$)] | 1.80 | 4.71 | |
| LS (1 week) [%] | 0.13% | 0.26% | |
| LS (2 weeks) [%] | 0.25% | 0.53% | |
| LS (4 weeks) [%] | 0.33% | 0.62% | |
| LS (8 weeks) [%] | 0.34% | 0.65% | |
| Adhesion (group a) [N] | 516 | 501 | 547 |
| Adhesion (group b) [N] | 98 | 0* | 539 |
| Adhesion (group c) [N] | 491 | 456 | 544 |
| Adhesion (group d) [N] | 371 | 321 | 540 |

*Debonding of all crowns during storage in water

In the following, the degree of conditioning for composite blocks according to Example 1 as described was determined in a time-dependent manner at 37° C. and 60° C.

TABLE 16

(Time-dependent degree of conditioning of Example 1):

|  | 37° C. | 60° C. |
|---|---|---|
| Degree of conditioning (1 week) [%] | 11% | 44% |
| Degree of conditioning (2 weeks) [%] | 16% | 65% |
| Degree of conditioning (3 weeks) [%] | 23% | 76% |
| Degree of conditioning (4 weeks) [%] | 25% | 82% |
| Degree of conditioning (5 weeks) [%] | 28% | 85% |
| Degree of conditioning (6 weeks) [%] | 31% | 87% |
| Degree of conditioning (7 weeks) [%] | 34% | 89% |
| Degree of conditioning (8 weeks) [%] | 36% | 91%* |
| Degree of conditioning (12 weeks) [%] | 44% | 93% |
| Degree of conditioning (16 weeks) [%] | 52% | 94% |
| Degree of conditioning (20 weeks) [%] | 59% | 95% |

*Adhesion measurements (groups c and d) carried out according to Table 3 with this degree of conditioning

TABLE 17

(Time-dependent degree of conditioning of Example 25):

|  | 37° C. | 60° C. |
|---|---|---|
| Degree of conditioning (1 week) [%] | 12% | 46% |
| Degree of conditioning (2 weeks) [%] | 18% | 66% |
| Degree of conditioning (3 weeks) [%] | 25% | 77% |
| Degree of conditioning (4 weeks) [%] | 27% | 83% |
| Degree of conditioning (5 weeks) [%] | 30% | 85% |
| Degree of conditioning (6 weeks) [%] | 32% | 87% |
| Degree of conditioning (7 weeks) [%] | 35% | 89% |
| Degree of conditioning (8 weeks) [%] | 38% | 91%* |
| Degree of conditioning (12 weeks) [%] | 43% | 92% |
| Degree of conditioning (16 weeks) [%] | 51% | 93% |
| Degree of conditioning (20 weeks) [%] | 57% | 94% |

*Adhesion measurements (groups c and d) carried out according to Table 15 with this degree of conditioning

TABLE 18

(Time-dependent degree of conditioning of Example 26):

|  | 37° C. | 60° C. |
|---|---|---|
| Degree of conditioning (1 week) [%] | 15% | 50% |
| Degree of conditioning (2 weeks) [%] | 20% | 70% |
| Degree of conditioning (3 weeks) [%] | 27% | 79% |
| Degree of conditioning (4 weeks) [%] | 29% | 84% |
| Degree of conditioning (5 weeks) [%] | 32% | 86% |
| Degree of conditioning (6 weeks) [%] | 34% | 87% |
| Degree of conditioning (7 weeks) [%] | 35% | 88% |
| Degree of conditioning (8 weeks) [%] | 38% | 90%* |
| Degree of conditioning (12 weeks) [%] | 42% | 91% |
| Degree of conditioning (16 weeks) [%] | 49% | 92% |
| Degree of conditioning (20 weeks) [%] | 55% | 93% |

*Adhesion measurements (groups c and d) carried out according to Table 15 with this degree of conditioning Supplementary Tests:

Based on the tests according to Examples 1, 25 and 26, supplementary tests were carried out in order to determine the dependency of certain measurement results for selected parameters on the degree of conditioning. The results of the further tests are shown in Tables 19, 20 and 21 below. The tables contain values in the respective columns with the heading "Unconditioned" and the respective right-hand columns with the headings "91%" or "90%" that are already found in Tables 3 (for Example 1) or 15 (for Examples 25 or 26). For the column "Unconditioned", there is therefore a correspondence for the lines from "3-point flexural strength" to "Adhesion (group b)". For the columns "91%" or "90%", there is a correspondence with respect to the lines "Adhesion (group c)" and "Adhesion (group d)".

All of the further entries in Tables 19 through 21 show results for the supplementary tests.

For the supplementary tests, composite blocks were stored at 60° C. in water until a respective degree of conditioning of (at least) 25%, 50%, 75% or 90% was reached in the weekly tests (see the above explanations on water treatment/conditioning of the composite blocks and determination of the degree of conditioning). The corresponding composite blocks with the adjusted degrees of conditioning were then subjected to the respective measurements.

Tables 19 through 21 show that 3-point flexural strength and E modulus respectively do not significantly depend on the degree of conditioning.

Water sorption ("$W_{SP}$") (determined analogously to EN ISO 4049:2009 (D) (7.12)) is a property that is independent of the actual water content or degree of conditioning of a composite block, as according to the measurement method, each sample specimen is first dried to constant mass and the water sorption is then related to this dried reference state. For this reason, the respective values for "$W_{SP}$" in Tables 19 through 21 remain the same (but of course vary among Examples 1, 25 and 26).

Tables 19 through 21 respectively also contain measurement results for the parameter "LS (8 weeks)". Provided that tests were conducted with preconditioned composite blocks (25%, 65%, 76% or 91%), in contrast to the above-described general determination method of the respective (preconditioned) sample specimens, drying to constant mass in the desiccator was not carried out, with the specimens being directly stored in water.

The results according to Tables 19 through 21 confirm that preconditioned composite blocks no longer swell as linearly as an unconditioned composite block. Swelling behavior is therefore not independent of the degree of preconditioning, but decreases with increasing preconditioning.

The following is to be noted with respect to the adhesion tests:

A comparison between group a) and group b) respectively shows that unconditioned blocks lose adhesion quality on storage in water (with the composition according to Example 1 being less susceptible than the compositions according to Examples 25 and 26). Preconditioning (to degrees of conditioning of 25%, 65%, 76% or 91%), i.e. on transition from group a) to group c), has no significant effect on the adhesion values achieved, which means that preconditioned composite blocks show direct adhesion that is equally favorable to that of unconditioned composite blocks.

When unconditioned or preconditioned blocks according to groups b) and d) are used and the idealised crowns produced therefrom, after bonding to the abutment, are stored for 8 weeks at 37° C. in water, the adhesion value for the unconditioned blocks is sharply reduced by storage in water compared to the groups a) or c) (e.g. according to Table 19 for Example 1, from 530 N (group a, without storage in water) to 411 N (group b, with storage in water)), while such storage in water in use of preconditioned blocks is significantly less detrimental. In each case, the composite blocks best retaining the adhesion properties are those preconditioned to a degree of conditioning of 90 or 91%, cf. Table 19 for Example 1: an adhesion value of 526 N (without storage in water after bonding of the crown), in contrast to the still excellent value of 501 N (determined after storage in water for 8 weeks after bonding of the crown). The tables thus impressively show that preconditioning causes a corresponding crown after bonding and after storage in water for 8 weeks to adhere significantly better to the corresponding abutment than a crown from a non-preconditioned composite block.

TABLE 19

(Example 1 with different degrees of conditioning):

| Degree of conditioning [%] | Unconditioned | 25% | 65% | 76% | 91% |
|---|---|---|---|---|---|
| 3-point flexural strength [MPa] | 274 | 276 | 271 | 269 | 270 |
| E modulus [GPa] | 18.3 | 18.3 | 18.2 | 18.1 | 17.9 |
| $W_{SP}$ [µg/mm³] | 13 | 13 | 13 | 13 | 13 |
| LS (8 weeks) [%] | 0.19% | 0.15% | 0.07% | 0.05% | 0.02% |
| Adhesion (group a) [N] | 530 | n.a. | n.a. | n.a. | n.a. |
| Adhesion (group b) [N] | 411 | n.a. | n.a. | n.a. | n.a. |
| Adhesion (group c) [N] | n.a. | 525 | 527 | 522 | 526 |
| Adhesion (group d) [N] | n.a. | 439 | 468 | 489 | 501 |

TABLE 20

(Example 25 with different degrees of conditioning):

| Degree of conditioning [%] | Unconditioned | 25% | 66% | 77% | 91% |
|---|---|---|---|---|---|
| 3-point flexural strength [MPa] | 201 | 195 | 202 | 193 | 198 |
| E modulus [GPa] | 11.1 | 11.1 | 11.0 | 10.8 | 10.5 |
| $W_{SP}$ [µg/mm³] | 20 | 20 | 20 | 20 | 20 |
| LS (8 weeks) [%] | 0.34% | 0.27% | 0.13% | 0.09% | 0.04% |
| Adhesion (group a) [N] | 516 | n.a. | n.a. | n.a. | n.a. |
| Adhesion (group b) [N] | 98 | n.a. | n.a. | n.a. | n.a. |
| Adhesion (group c) [N] | n.a. | 510 | 501 | 498 | 491 |
| Adhesion (group d) [N] | n.a. | 128 | 278 | 339 | 371 |

TABLE 21

(Example 26 with different degrees of conditioning):

| Degree of conditioning [%] | Unconditioned | 27% | 50% | 79% | 90% |
|---|---|---|---|---|---|
| 3-point flexural strength [MPa] | 129 | 127 | 123 | 118 | 109 |
| E modulus [GPa] | 8.7 | 8.6 | 8.4 | 8.1 | 7.5 |
| $W_{SP}$ [µg/mm³] | 41 | 41 | 41 | 41 | 41 |
| LS (8 weeks) [%] | 0.65% | 0.50% | 0.34% | 0.15% | 0.08% |
| Adhesion (group a) [N] | 501 | n.a. | n.a. | n.a. | n.a. |
| Adhesion (group b) [N] | 0 | n.a. | n.a. | n.a. | n.a. |
| Adhesion (group c) [N] | n.a. | 496 | 482 | 473 | 456 |
| Adhesion (group d) [N] | n.a. | 39 | 117 | 222 | 321 |

The invention claimed is:

1. Milling blank for producing an indirect dental restoration,
    composed of a cured resin-based composite and 10 wt % to 25 wt % of silica based on the total mass of the milling blank,
    wherein the milling blank is preconditioned such that the milling blank contains water in an amount of at least 25% of the water sorption $W_{sp}$,
    wherein the resin-based composite comprises an inorganic filler a),
    wherein the inorganic filler a) comprises a glass composition a1), and
    wherein the glass composition a1) comprises a first glass composition a1a) with a D50 value in the range of 0.4 to 1.0 µm.

2. Milling blank according to claim 1, containing water in an amount of at least 50% of the water sorption $W_{sp}$.

3. Milling blank according to claim 1, with an E modulus determined according to ADA Specification No. 27—1993 of at least 10 GPa.

4. Milling blank according to claim 1, with a water sorption $W_{sp}$ of at most 40 µg/mm³.

5. Milling blank according to claim 1, wherein the quotient of the water sorption $W_{sp}$ and the E modulus determined according to ADA Specification No. 27-1993 is less than 1.35 µg/(GPa×mm³).

6. Milling blank according to claim 1, wherein the
    inorganic filler a) is present in an amount of at least 70 wt. %, based on the total mass of the milling blank
    and
    the resin-based composite further comprises a resin matrix b).

7. Milling blank according to claim 6, wherein the inorganic filler a) further comprises
    a component a2) comprising non-aggregated and non-agglomerated silica with an average particle size of not more than 80 nm.

8. Milling blank according to claim 7, wherein the glass composition a1) further comprises
    a second glass composition a1b) with a D50 value in the range of 1.2 to 5.0 µm,
    wherein the mass ratio of a1a) to a1b) is between 1:1.5 and 1:8, wherein the mass ratio of a2) to the total of a1a) and a1b) is between 1:3 and 1:6,
    wherein the ratio of the D50 value of the first glass composition a1a) to the D50 value of the second glass composition a1b) is in the range of 1:1.5 to 1:10, and wherein the D75 value of the first glass composition a1a) is less than the D25 value of the second glass composition a1b).

9. Milling blank according to claim 6, wherein the resin matrix b) is a polymer of monomers that contains difunctional (meth)acrylates,
   wherein the difunctional (meth)acrylates comprise ethoxylated bisphenol A dimethacrylate with an average degree of ethoxylation of 2 to 4 ethoxy groups per molecule;
   wherein the percent by weight of ethoxylated bisphenol A dimethacrylate with an average degree of ethoxylation of 2 to 4 ethoxy groups per molecule is greater than 40 wt. % and less than 50 wt. %, based on the total mass of the monomers.

10. Milling blank according to claim 6, wherein the difference between the water sorption $W_{sp}$ and the water content of the milling blank is less than 10 μg/mm³.

11. Milling blank according to claim 6, the dimensions of which are selected such that
   a cube with an edge length of 10 mm,
   and/or
   a cuboid having a square base with an edge length of 10 mm, and a height of 20 mm can be milled from it.

12. Milling blank according to claim 1, wherein the milling blank is sealed or enclosed in a water-tight manner.

13. A method of producing a moulded part for use as an indirect dental restoration comprising:
   providing a milling blank according to claim 1 to produce the moulded part.

14. Method for producing a milling blank according to claim 1 or a moulded part produced therefrom for use as an indirect dental restoration, comprising the following steps:
   (i) production or provision of a milling blank containing water in an amount of less than 25% of the water sorption $W_{sp}$,
   (ii) adjustment of the conditions in which the milling blank provided or produced in step (i) sorbs water and maintenance of these conditions until the milling blank contains water in an amount of at least 25% of the water sorption $W_{sp}$ and water-tight sealing or enclosing of the milling blank produced.

15. Method according to claim 14 for producing a moulded part for use as an indirect dental restoration, comprising the following additional step:
   (iii) milling of the moulded part from the milling blank produced in step (ii).

16. Milling blank according to claim 1, wherein the milling blank is preconditioned by addition of water.

* * * * *